(12) United States Patent
Vite et al.

(10) Patent No.: US 6,916,815 B2
(45) Date of Patent: Jul. 12, 2005

(54) C-6 MODIFIED INDAZOLYLPYRROLOTRIAZINES

(75) Inventors: Gregory D. Vite, Titusville, NJ (US); Ashvinikumar V. Gavai, Princeton Junction, NJ (US); Brian E. Fink, Princeton Junction, NJ (US); Harold Mastalerz, Guilford, CT (US); John F. Kadow, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/736,476

(22) Filed: Dec. 15, 2003

(65) Prior Publication Data

US 2004/0142931 A1 Jul. 22, 2004

Related U.S. Application Data

(60) Provisional application No. 60/433,190, filed on Dec. 13, 2002.

(51) Int. Cl.$^7$ ............... C07D 487/02; A61K 31/53; A61P 19/02
(52) U.S. Cl. ................................... 514/243; 544/183
(58) Field of Search .................. 544/183; 514/243, 514/242

(56) References Cited

FOREIGN PATENT DOCUMENTS

| WO | 778 277 A1 | 6/1997 |
|---|---|---|
| WO | WO 98/08847 | 3/1998 |
| WO | WO 01/14378 | 3/2001 |
| WO | WO 02/40486 A2 | 5/2002 |

OTHER PUBLICATIONS

Cecil Textbook of Medicine, edited by Bennet, J.C., and Plum F., 20th edition,vol. 1, 1004–1010, 1996.*
Mass, R. D., Int. J. Radiation Oncology Bio. Phys.vol. 58(3): 932–940, 2004.*
Fabbro et al. Pharmacology & therapeutics 93, 79–98, 2002.*
Otter et al., "Conformational Properties of Purine–Like C–Nucleosides", Nucleoside & Nucleotides, vol. 15, Nos. 1–3, pp. 793–807 (1996).

Quintella et al., "A Ready One–Pot Preparation for Pyrrolo [2,1-fl-[1,2,4] Triazine and Pyrazolo[5,1-c]Pyramidol[4, 5-e]-[1,2,4]Triazine Derivatives", Tetrahedron, vol. 52, No. 8, pp. 3037–3048 (1996).
Patil et al., "Synthesis of Pyrrolo [2,1-f][1,2,4] Triazine Congeners of Nucleic Acid Purines via the N–Amination of 2–Substituted Pyrroles [1]", J. Heterocyclic Chem. vol. 31, No. 4, 781–807 (1994).
Neunhoeffer et al., "Cycloadditionen mit Methoxy–und Dialkylamino–1,2,4–Triazinen", Justus Liebigs Ann. Chem., vol. 9, pp. 1413–1420 (1977) & Chem. Abstract 88:121113q, (1978).
Skobe et al., "Halting Angiogenesis Suppresses Carcinoma Cell Invasion". Nature Medicine, vol. 3, No. 11, pp. 1223–1227 (1997).

* cited by examiner

*Primary Examiner*—Venkataraman Balasubramanian
(74) *Attorney, Agent, or Firm*—Elliott Korsen

(57) ABSTRACT

The present invention provides compounds of formula I

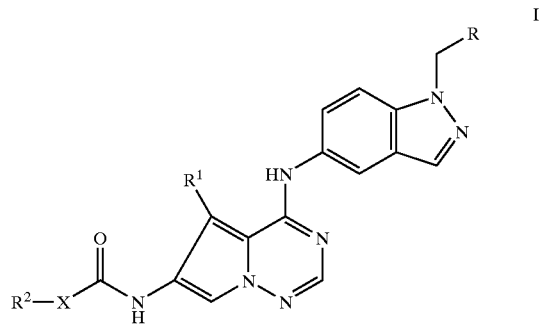

and pharmaceutically acceptable salts thereof.

The formula I compounds inhibit tyrosine kinase activity of growth factor receptors such as HER1, HER2 and HER4 thereby making them useful as antiproliferative agents. The formula I compounds are also useful for the treatment of other diseases associated with signal transduction pathways operating through growth factor receptors.

10 Claims, No Drawings

C-6 MODIFIED INDAZOLYLPYRROLOTRIAZINES

This application claims the priority benefit of U.S. Provisional Application No. 60/433,190 filed Dec. 13, 2002, the disclosures of which are incorporated herein by reference in their entirety.

FIELD OF THE INVENTION

This invention relates to compounds that inhibit the tyrosine kinase activity of growth factor receptors such as HER1, HER2, and HER4 thereby making them useful as anti-cancer agents. The compounds are also useful in the treatment of diseases, other than cancer, which are associated with signal transduction pathways operating through growth factor receptors such as HER1, HER2 and HER4.

BACKGROUND OF THE INVENTION

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain.

The human epidermal growth factor receptor (HER) family consists of four distinct receptor tyrosine kinases referred to HER1, HER2, HER3, and HER4. These kinases are also referred to as erbB1, erbB2, etc. HER1 is also commonly referred to as the epidermal growth factor (EGF) receptor. With the exception of HER3, these receptors have intrinsic protein kinase activity that is specific for tyrosine residues of phosphoacceptor proteins. The HER kinases are expressed in most epithelial cells as well as tumor cells of epithelial origin. They are also often expressed in tumor cells of mesenchymal origin such as sarcomas or rhabdomyosarcomas. RTKs such as HER1 and HER2 are involved in cell proliferation and are associated with diseases such as psoriasis and cancer. Disruption of signal transduction by inhibition of these kinases would have an antiproliferative and therapeutic effect.

The enzymatic activity of receptor tyrosine kinases can be stimulated by either overexpression, or by ligand-mediated dimerization. The formation of homodimers as well as heterodimers has been demonstrated for the HER receptor family. An example of homodimerization is the dimerization of HER1 (EGF receptor) by one of the EGF family of ligands (which includes EGF, transforming growth factor alpha, betacellulin, heparin-binding EGF, and epiregulin). Heterodimerization among the four HER receptor kinases can be promoted by binding to members of the heregulin (also referred to neuregulin) family of ligands. Such heterodimerization as involving HER2 and HER3, or a HER3/HER4 combination, results in a significant stimulation of the tyrosine kinase activity of the receptor dimers even though one of the receptors (HER3) is enzymatically inert. The kinase activity of HER2 has been shown to be activated also by virtue of overexpression of the receptor alone in a variety of cell types. Activation of receptor homodimers and heterodimers results in phosphorylation of tyrosine residues on the receptors and on other intracellular proteins. This is followed by the activation of intracellular signaling pathways such as those involving the microtubule associated protein kinase (MAP kinase) and the phosphatidylinositol 3-kinase (PI3 kinase). Activation of these pathways have been shown to lead to cell proliferation and the inhibition of apoptosis. Inhibition of HER kinase signaling has been shown to inhibit cell proliferation and survival.

SUMMARY OF THE INVENTION

The compounds of the invention inhibit the tyrosine kinase activity of growth factor receptors such as HER1, HER2, and HER4 and as such, can be used to treat diseases that are associated with signal transduction pathways operating through growth factor receptors. For example the compounds of the instant invention can be used as antiproliferatives and anticancer agents. More specifically, the invention comprises a compound of formula I

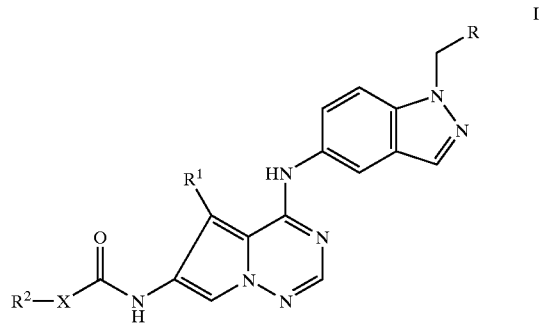

wherein

R is selected from the group consisting of aryl, substituted aryl, heterocyclo, and substituted heterocyclo;

$R^1$ is selected from the group consisting of alkyl and substituted alkyl;

$R^2$ is selected from the group consisting of hydrogen, alkyl, substituted alkyl, cycloalkyl, substituted cycloalkyl, aryl, substituted aryl, aralkyl, heterocyclo, and substituted heterocyclo; or, $R^2$ may be absent;

X is selected from the group consisting of a bond, O, S, $C(R^3)_2$, $C(R^3)_3$, $NR^3$; and $N(R^3)_2$;

$R^3$ is independently selected from the group consisting of hydrogen, alkyl, substituted alkyl, aryl, substituted aryl, aralkyl, heterocyclo, and substituted heterocyclo, and pharmaceutically acceptable salts, prodrugs, enantiomers, diastereomers, and solvates thereof.

Also provided for is a method for treating proliferative diseases, comprising administering to a warm-blooded species in need thereof, a therapeutically effective amount of a compound of formula I.

DETAILED DESCRIPTION OF THE INVENTION

The present invention provides for compounds of formula I, pharmaceutical compositions employing such compounds and for methods of using such compounds.

More specifically, the present invention includes compounds of formula I

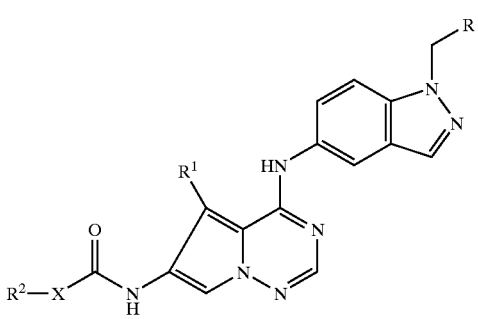

wherein
R is selected from the group consisting of aryl, substituted aryl, heterocyclo, and substituted heterocyclo;
$R^1$ is selected from the group consisting of alkyl and substituted alkyl;
$R^2$ is selected from the group consisting of hydrogen, alkyl, substituted alkyl, cycloalkyl, substituted cycloalkyl, aryl, substituted aryl, aralkyl, heterocyclo, and substituted heterocyclo; or, $R^2$ may be absent;
X is selected from the group consisting of a bond, O, S, $C(R^3)_2$, $C(R^3)_3$, $NR^3$; and $N(R^3)_2$;
$R^3$ is independently selected from the group consisting of hydrogen, alkyl, substituted alkyl, aryl, substituted aryl, aralkyl, heterocyclo, and substituted heterocyclo,
and pharmaceutically acceptable salts, prodrugs, enantiomers, diastereomers, and solvates thereof.

Preferred alkyl, substituted alkyl, aryl, substituted aryl, aralkyl, heterocyclo, and substituted heterocyclo groups for $R^2$ include, but are not limited to, the following:
benzyl, imidazolyl-ethyl, (methyl-imidazolyl)-ethyl, piperidinyl-ethyl, pyridinyl-propyl, pyridinyl-methyl, morpholinyl-ethyl, (methyl-imidazolyl)-methyl, pyridinyl-ethyl, amino-piperidinyl-methyl, 4-amino-1-methyl-piperidin-3-ol, (methyl-piperazinyl)-ethyl, pyridinyl-ethyl, (methyl-piperidinyl)-ethyl, (methyl-imidazolyl)-propyl, (methyl-piperidinyl)-methyl, (methyl-piperazinyl)-propyl, diisopropylamino-ethyl, piperidinyl-propyl, dimethylamino-ethyl, dimethylamino-propyl, [(trifluoro-acetyl)-piperidinyl]-propyl, piperidinyl-ethyl, piperazinyl-ethyl, piperazinyl-propyl, pyrrolidinyl-ethyl, triazolyl-ethyl, triazolyl-propyl, (dimethylamino-ethoxy)-ethyl, imidazolyl-propyl, [(trifluoro-acetyl)-piperidinyl]-propyl, (piperazinyl-ethoxy)-ethyl, [(trifluoro-acetyl)-piperazinyl]-propyl, [(trifluoro-acetyl)-piperazinyl]-ethyl, piperidinyl-methyl, pyrazolyl-ethyl, (amino-ethoxy)-ethyl, (methoxy-ethoxy)-ethyl, pyrazolyl-propyl, [(methoxy-ethyl)-methyl-amino]-ethyl, morpholinyl-propyl, (cyanomethyl-piperazinyl)-ethyl, [(cyano-ethyl)-methyl-amino]-ethyl, [(methoxy-ethyl)-piperidinyl]-methyl, [(methoxy-ethyl)-piperidinyl]-ethyl, [(fluoro-ethyl)-methyl-amino]-ethyl, [(fluoro-ethyl)-methyl-amino]-propyl, (methyl-piperidinyl)-propyl, [(methanesulfonyl-ethyl)-piperazinyl]-ethyl, [(cyano-ethyl)-piperazinyl]-ethyl, [(methoxy-ethyl)-piperazinyl]-ethyl, [(methoxy-ethyl)-methyl-amino]-propyl, (cyanomethyl-methyl-amino)-propyl, (cyanomethyl-methyl-amino)-ethyl, [(methanesulfonyl-ethyl)-methyl-amino]-propyl, (difluoro-piperidinyl)-propyl, (difluoro-piperidinyl)-ethyl, [(cyano-ethyl)-methyl-amino]-propyl, [(methanesulfonyl-ethyl)-methyl-amino]-ethyl, [(trifluoro-ethyl)-piperazinyl]-ethyl, [cyanomethyl-(methanesulfonyl-ethyl)-amino]-propyl, [cyanomethyl-(methanesulfonyl-ethyl)-amino]-ethyl, (cyanomethyl-piperazinyl)-propyl, [(methanesulfonyl-ethyl)-piperazinyl]-propyl, [(cyano-ethyl)-piperazinyl]-propyl, [(trifluoro-ethyl)-piperazinyl]-propyl, (methanesulfonyl-ethyl-amino)-ethyl, [(cyano-ethyl)-piperidinyl]-methyl, (cyanomethyl-piperidinyl)-methyl, (hydroxy-piperidinyl)-propyl, [(methanesulfonyl-ethyl)-piperidinyl]-methyl, piperidinyl-methyl, piperidinyl, imidazolyl-propyl, 1-methyl-[1,4]-diazepan-6-ol, methanesulfonyl-propyl, (methanesulfonyl-ethyl-amino)-propyl, pyrrolidinyl-methyl, methanesulfonyl-ethyl, (cyanomethyl-amino)-ethyl, (cyanomethyl-amino)-propyl, (dioxo-thiomorpholinyl)-propyl, (oxo-piperidinyl)-propyl, [(difluoro-ethyl)-methyl-amino]-ethyl, morpholinyl-methyl, (hydroxy-pyrrolidinyl)-propyl, (hydroxy-piperidinyl)-propyl, pyrrolidinyl-methyl, (hydroxy-pyrrolidinyl)-propyl, methyl-piperidinyl, (methyl-pyrrolidinyl)-methyl, morpholinyl-methyl, pyrrolidinyl-methyl, (methyl-tetrahydro-pyridinyl)-methyl, (cyano-ethyl)-piperidinyl, azetidinyl, (methanesulfonyl-ethyl)-piperidinyl, (cyano-methyl)-piperidinyl, isopropyl-piperidinyl, propyl-piperidinyl, acetyl-piperidinyl, ethyl-piperidinyl, allyl-piperidinyl, tetrahydro-pyranyl, (hydroxy-ethyl)-piperidinyl, (methyl-pyrrolidinyl)-methyl, (methoxyethyl)-piperidinyl, piperidinyl, (methoxy-ethyl)-azetidinyl, (methoxy-methoxymethyl-ethyl)-piperidinyl, (methoxy-acetyl)-piperidinyl, methoxycarbonyl-piperidnyl, (hydroxy-acetyl)-piperidinyl, piperidine-carboxylic acid-acetoxy-ethyl, piperidine-carboxylic acid-acetoxy-methyl-ethyl, hydroxy-piperidinyl, amino-cyclohexyl, piperidinyl, piperidine-carboxylic acid-methyl-oxo-dioxolylmethyl, hydroxymethyl-piperidinyl, (aminomethyl)-cyclohexyl, amino-methyl-cyclohexyl, hydroxy-piperidinyl-methyl, morpholinyl, amino-cyclohexyl, hydroxymethyl-piperidinyl, tetrahydro-pyranyl, methanesulfonyl-propyl, amino-methyl-propyl, amino-cyclohexyl, amino-methyl-cyclohexyl, (hydroxy-piperidinyl)-propyl, piperidinyl, amino-propyl, morpholinyl-methyl, piperidinyl, (tert-butoxycarbonyl-morpholinyl)-methyl, benzyl, imidazolyl-ethyl, piperidinyl-ethyl, methoxyethyl, (diethylamino)-(methoxyethyl), pyrrolidinyl-ethyl, acetamide and methyl.

Preferred aryl, substituted aryl, heterocyclo, and substituted heterocyclo groups for R include, but are not limited to, the following:
oxazolyl, thienyl, pyridinyl, thiazolyl, pyrazinyl, and phenyl, all of which may be suitably substituted with one or more substitutents.

In a preferred embodiment, the invention comprises a compound of formula I wherein R is aryl or substituted aryl and $R^1$ is a lower alkyl group. In a more preferred embodiment $R^1$ is methyl or ethyl.

In another preferred embodiment, the invention comprises a compound of formula I wherein X is —O— and $R^2$ is cycloalkyl, substituted cycloalkyl, heterocyclo or substituted heterocyclo.

In yet another preferred embodiment, the invention comprises a compound of formula I wherein R is phenyl or substituted phenyl and $R^1$ is methyl or ethyl.

Preferred compounds of the instant invention include the following
[5-ethyl-4-[[(1-phenylmethyl)-1H-indazol-5-yl]amino]pyrrolo[2,1-f][1,2,4]triazin-6-yl]-carbamic acid, (3S)-3-morpholinylmethyl ester,

[5-ethyl-4-[[(1-phenylmethyl)-1H-indazol-5-yl]amino]pyrrolo[2,1-f][1,2,4]triazin-6-yl]-carbamic acid, (2R)-2-pyrrolidinylmethyl ester,

[5-ethyl-4-[[(1-phenylmethyl)-1H-indazol-5-yl]amino]pyrrolo[2,1-f][1,2,4]triazin-6-yl]-carbamic acid, (2S)-2-pyrrolidinylmethyl ester,

[5-ethyl-4-[[(1-phenylmethyl)-1H-indazol-5-yl]amino]pyrrolo[2,1-f][1,2,4]triazin-6-yl]-carbamic acid, (3R)-3-morpholinylmethyl ester,

[5-ethyl-4-[[(1-phenylmethyl)-1H-indazol-5-yl]amino]pyrrolo[2,1-f][1,2,4]triazin-6-yl]-carbamic acid, 3-[(3S)-3-hydroxy-1-pyrrolidinyl]propyl ester,

[5-ethyl-4-[[(1-phenylmethyl)-1H-indazol-5-yl]amino]pyrrolo[2,1-f][1,2,4]triazin-6-yl]-carbamic acid, 3-[(3S)-3-hydroxy-1-piperidinyl]propyl ester,

[5-ethyl-4-[[(1-phenylmethyl)-1H-indazol-5-yl]amino]pyrrolo[2,1-f][1,2,4]triazin-6-yl]-carbamic acid, (3R)-3-pyrrolidinylmethyl ester,

[5-ethyl-4-[[(1-phenylmethyl)-1H-indazol-5-yl]amino]pyrrolo[2,1-f][1,2,4]triazin-6-yl]-carbamic acid, 3-[(3R)-3-hydroxy-1-pyrrolidinyl]propyl ester,

[5-ethyl-4-[[(1-phenylmethyl)-1H-indazol-5-yl]amino]pyrrolo[2,1-f][1,2,4]triazin-6-yl]-carbamic acid, [(2S)-1-methyl-2-pyrrolidinyl]methyl ester,

[5-ethyl-4-[[(1-phenylmethyl)-1H-indazol-5-yl]amino]pyrrolo[2,1-f][1,2,4]triazin-6-yl]-carbamic acid, (2S)-2-morpholinylmethyl ester,

[5-ethyl-4-[[(1-phenylmethyl)-1H-indazol-5-yl]amino]pyrrolo[2,1-f][1,2,4]triazin-6-yl]-carbamic acid, (3S)-3-pyrrolidinylmethyl ester,

[5-ethyl-4-[[(1-phenylmethyl)-1H-indazol-5-yl]amino]pyrrolo[2,1-f][1,2,4]triazin-6-yl]-carbamic acid, (2R)-2-morpholinylmethyl ester,

[5-ethyl-4-[[(1-phenylmethyl)-1H-indazol-5-yl]amino]pyrrolo[2,1-f][1,2,4]triazin-6-yl]-carbamic acid, [(3R)-1-methyl-3-pyrrolidinyl]methyl ester,

[5-ethyl-4-[[(1-phenylmethyl)-1H-indazol-5-yl]amino]pyrrolo[2,1-f][1,2,4]triazin-6-yl]-carbamic acid, trans-4-aminocyclohexyl ester,

[5-ethyl-4-[[(1-phenylmethyl)-1H-indazol-5-yl]amino]pyrrolo[2,1-f][1,2,4]triazin-6-yl]-carbamic acid, (3R)-3-piperidinyl ester,

[5-ethyl-4-[[(1-phenylmethyl)-1H-indazol-5-yl]amino]pyrrolo[2,1-f][1,2,4]triazin-6-yl]-carbamic acid, (3S)-3-piperidinyl ester,

[5-ethyl-4-[[(1-phenylmethyl)-1H-indazol-5-yl]amino]pyrrolo[2,1-f][1,2,4]triazin-6-yl]-carbamic acid, cis-4-aminocyclohexyl,

[5-ethyl-4-[[(1-phenylmethyl)-1H-indazol-5-yl]amino]pyrrolo[2,1-f][1,2,4]triazin-6-yl]-carbamic acid, (2R,4R)-2-(hydroxymethyl)-4-piperidinyl ester,

[5-ethyl-4-[[(1-phenylmethyl)-1H-indazol-5-yl]amino]pyrrolo[2,1-f][1,2,4]triazin-6-yl]-carbamic acid, (2S)-2-(hydroxymethyl)-4-piperidinyl ester,

[5-ethyl-4-[[(1-phenylmethyl)-1H-indazol-5-yl]amino]pyrrolo[2,1-f][1,2,4]triazin-6-yl]-carbamic acid, cis-4-(aminomethyl)cyclohexyl ester,

[5-ethyl-4-[[(1-phenylmethyl)-1H-indazol-5-yl]amino]pyrrolo[2,1-f][1,2,4]triazin-6-yl]-carbamic acid, cis-4-amino-4-methylcyclohexyl ester,

[5-ethyl-4-[[(1-phenylmethyl)-1H-indazol-5-yl]amino]pyrrolo[2,1-f][1,2,4]triazin-6-yl]-carbamic acid, [(2R,4R)-4-(hydroxy-2-piperidinyl]methylester,

[5-ethyl-4-[[(1-phenylmethyl)-1H-indazol-5-yl]amino]pyrrolo[2,1-f][1,2,4]triazin-6-yl]-carbamic acid, trans-4-(aminomethyl)cyclohexyl ester,

[5-ethyl-4-[[1-(2-oxazolylmethyl)-1H-indazol-5-yl]amino]pyrrolo[2,1-f][1,2,4]triazin-6-yl]-carbamic acid, (3S)-3-morpholinylmethyl ester,

[5-ethyl-4-[[1-(2-thienylmethyl)-1H-indazol-5-yl]amino]pyrrolo[2,1-f][1,2,4]triazin-6-yl]-carbamic acid, (3S)-3-morpholinylmethyl ester,

[5-ethyl-4-[[1-[(3-fluorophenyl)methyl]-1H-indazol-5-yl]amino]pyrrolo[2,1-f][1,2,4]triazin-6-yl]-carbamic acid, (3S)-3-morpholinylmethyl ester,

[5-ethyl-4-[[1-(4-thiazolylmethyl)-1H-indazol-5-yl]amino]pyrrolo[2,1-f][1,2,4]triazin-6-yl]-carbamic acid, (3S)-3-morpholinylmethyl ester,

[5-ethyl-4-[[1-(3-thienylmethyl)-1H-indazol-5-yl]amino]pyrrolo[2,1-f][1,2,4]triazin-6-yl]-carbamic acid, (3S)-3-morpholinylmethyl ester,

[5-ethyl-4-[[1-(2-pyridinylmethyl)-1H-indazol-5-yl]amino]pyrrolo[2,1-f][1,2,4]triazin-6-yl]-carbamic acid, (3S)-3-morpholinylmethyl ester,

[5-ethyl-4-[[1-(2-thiazolylmethyl)-1H-indazol-5-yl]amino]pyrrolo[2,1-f][1,2,4]triazin-6-yl]-carbamic acid, (3S)-3-morpholinylmethyl ester,

[5-ethyl-4-[[1-(3-pyridinylmethyl)-1H-indazol-5-yl]amino]pyrrolo[2,1-f][1,2,4]triazin-6-yl]-carbamic acid, (3S)-3-morpholinylmethyl ester,

[5-ethyl-4-[[1-(pyrazinylmethyl)-1H-indazol-5-yl]amino]pyrrolo[2,1-f][1,2,4]triazin-6-yl]-carbamic acid, (3S)-3-morpholinylmethyl ester,

[4-[[1-(3-fluorophenyl)methyl]-1H-indazol-5-ylamino]-5-methyl-pyrrolo[2,1-f][1,2,4]triazin-6-yl]-carbamic acid, trans-4-aminocyclohexyl ester,

[4-[[1-(3-fluorophenyl)methyl]-1H-indazol-5-ylamino]-5-methyl-pyrrolo[2,1-f][1,2,4]triazin-6-yl]-carbamic acid, (2R,4R)-2-(hydroxymethyl)-4-piperidinyl ester,

[4-[[1-(3-fluorophenyl)methyl]-1H-indazol-5-ylamino]-5-methyl-pyrrolo[2,1-f][1,2,4]triazin-6-yl]-carbamic acid, (2S,4S)-2-(hydroxymethyl)-4-piperidinyl ester,

[4-[[1-(3-fluorophenyl)methyl]-1H-indazol-5-ylamino]-5-methyl-pyrrolo[2,1-f][1,2,4]triazin-6-yl]-carbamic acid, cis-4-aminocyclohexyl ester,

[4-[[1-(3-fluorophenyl)methyl]-1H-indazol-5-ylamino]-5-methyl-pyrrolo[2,1-f][1,2,4]triazin-6-yl]-carbamic acid, cis-4-amino-4-methyl-cyclohexyl ester,

[4-[[1-(3-fluorophenyl)methyl]-1H-indazol-5-ylamino]-5-methyl-pyrrolo[2,1-f][1,2,4]triazin-6-yl]-carbamic acid, (2R)-2-aminopropyl ester,

[4-[[1-(3-fluorophenyl)methyl]-1H-indazol-5-ylamino]-5-methyl-pyrrolo[2,1-f][1,2,4]triazin-6-yl]-carbamic acid, (2S)-2-aminopropyl ester,

[4-[[1-(3-fluorophenyl)methyl]-1H-indazol-5-ylamino]-5-methyl-pyrrolo[2,1-f][1,2,4]triazin-6-yl]-carbamic acid, (3S)-3-morpholinylmethyl ester,

[4-[[1-(3-fluorophenyl)methyl]-1H-indazol-5-ylamino]-5-methyl-pyrrolo[2,1-f][1,2,4]triazin-6-yl]-carbamic acid, (3R)-3-piperidinyl ester,

[4-[[1-(3-fluorophenyl)methyl]-1H-indazol-5-ylamino]-5-methyl-pyrrolo[2,1-f][1,2,4]triazin-6-yl]-carbamic acid, (3S)-3-piperidinyl ester, 3-[[[[[4-[[1-[(3-fluorophenyl)methyl]-1H-indazol-5-yl]amino]-5-methylpyrrolo[2,1-f][1,2,4]triazin-6-yl]amino]carbonyl]oxy]methyl]-4-morpholinecarboxylic acid, (3S)-1,1-dimethylethyl ester,

[4-[[1-(3-fluorophenyl)methyl]-1H-indazol-5-ylamino]-5-methyl-pyrrolo[2,1-f][1,2,4]triazin-6-yl]-carbamic acid, 3-morpholinylmethyl ester, and

[4-[[1-(3-fluorophenyl)methyl]-1H-indazol-5-ylamino]-5-methyl-pyrrolo[2,1-f][1,2,4]triazin-6-yl]-carbamic acid, (3R)-3-morpholinylmethyl ester.

Preferred compounds of the instant invention exhibit $IC_{50}$ values of less than 5 $\mu$M in one or more of HER1, HER2 and HER4 assays. More preferred are compounds have less than 1 μM assay activity. Even more preferred are compounds having less than 0.1 μM assay activity.

Due to the possible negative side effect of life-threatening ventricular arrhythmia, compounds having low HERG (Human Ether-a-go-go Related Gene) patch-clamp assay activity are desirable. Preferred compounds have $IC_{50}$ values in the HERG assay of greater than 1 μM.

Definitions

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino, heterocyclo, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclo. Where noted above where the substituent is further substituted it will be with alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl or a substituted aryl group bonded directly through an alkyl group, such as benzyl.

The term "substituted aryl" refers to an aryl group substituted by, for example, one to four substituents such as alkyl, substituted alkyl, alkenyl, substituted alkenyl, alkynyl, substituted alkynyl, aryl, substituted aryl, aralkyl, halo, trifluoromethoxy, trifluoromethyl, hydroxy, alkoxy, alkanoyl, alkanoyloxy, aryloxy, aralkyloxy, amino, alkylamino, arylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or aralkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclo, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$–$C_7$ carbocylic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, homopiperazinyl, 2-oxohomopiperazinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1, 1-dioxothienyl, dioxanyl, isothiazolidinyl, thietanyl, thiiranyl, triazinyl, and triazolyl, and the like.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, indazolyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary heterocyclo substituents include one or more alkyl or aralkyl groups, as described above, or one or more groups described above as alkyl substituents as well as alkylsulfonyl groups and haloacetyl groups. Also included are smaller heterocyclos, such as, epoxides and aziridines. Preferred substituted heterocycles are shown is the examples of this specification.

The term "carbocyclic ring" refers to stable, saturated or partially unsaturated monocyclic hydrocarbon rings of 3 to 7 carbon atoms such as cyclopropyl, cyclobutyl, cyclopentyl, cyclohexyl and cycloheptyl. The term "optionally substituted" as it refers to "carbocyclic ring" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatoms" shall include oxygen, sulfur and nitrogen.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the formula I may also have prodrug forms. Any compound that will be converted in vivo to provide the bioactive agent (i.e., the compound for formulas I) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol.42, p. 309–396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, p. 113–191 (1991);

c) H. Bundgaard, *Advanced Drug Delivery Reviews*, 8, 1–38 (1992);

It should further be understood that solvates (e.g., hydrates) of the compounds of formula I are also with the scope of the present invention. Methods of solvation are generally known in the art.

Use and Utility

The present invention is based on the discovery that certain pyrrolotriazines are inhibitors of protein kinases. More specifically, pyrrolotriazines such as those described in this invention inhibit the protein tyrosine kinase activity of members of the HER family of receptors. These inhibitors will be useful in the treatment of proliferative diseases that are dependent on signaling by one or more of these receptors. Such diseases include psoriasis, rheumatoid arthritis, and solid tumors of the lung, head and neck, breast, colon, ovary, and prostate. The invention relates to a pharmaceutical composition of compound of formula I, or pharmaceutically acceptable salt or hydrate thereof, and a pharmaceutically acceptable carrier in the treatment of hyperproliferative disorder in mammal. In particular, the said pharmaceutical composition is expected to inhibit the growth of those primary and recurrent solid tumors which are associated with HER1 (EGF receptor) and HER2, especially those tumors which are significantly dependent on HER1 or HER2 for their growth and spread, including for example, cancers of the bladder, squamous cell, head, colorectal, oesophageal, gynecological (such as ovarian), pancreas, breast, prostate, vulva, skin, brain, genitourinary tract, lymphatic system (such as thyroid), stomach, larynx and lung. In another embodiment, the compounds of the present invention are also useful in the treatment of non-cancerous disorders such as psoriasis and rheumatoid arthritis.

Thus according to a further aspect of the invention there is provided the use of a compound of the formula I, or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of formula I or a pharmaceutically acceptable salt thereof as defined herein before.

By virtue of their ability to inhibit HER1, HER2 and HER4 kinases, compounds of the present invention can be used for the treatment of proliferative diseases, including psoriasis and cancer. The HER1 receptor kinase has been shown to be expressed and activated in many solid tumors including head and neck, prostate, non-small cell lung, colorectal, and breast cancer. Similarly, the HER2 receptor kinase has been shown to be overexpressed in breast, ovarian, lung and gastric cancer. Monoclonal antibodies that downregulate the abundance of the HER2 receptor or inhibit signaling by the HER1 receptor have shown anti-tumor effficacy in preclincal and clinical studies. It is therefore expected that inhibitors of the HER1 and HER2 kinases will have efficacy in the treatment of tumors that depend on signaling from either of the two receptors. In addition, these compounds will have efficacy in inhibiting tumors that rely on HER receptor heterodimer signaling. These compounds are expected to have efficacy either as single agent or in combination (simultaneous or sequentially) with other chemotherapeutic agens such as Taxol, adriamycin, and cisplatin. Since HER1 and HER2 signaling has been shown to regulate expression of angiogenic factors such as vascular endothelial growth factor (VEGF) and interleukin 8 (IL8), these compounds are expected to have anti-tumor efficacy resulting from the inhibition of angiogenesis in addition to the inhibition of tumor cell proliferation and survival. The HER2 receptor has been shown to be involved in the hyperproliferation of synovial cells in rheumatoid arthritis, and may contribute to the angiogenic component of that inflammatory disease state. The inhibitors described in this invention are therefore expected to have efficacy in the treatment of rheumatoid arthritis. The ability of these compounds to inhibit HER1 further adds to their use as anti-angiogenic agents. See the following documents and references cited therein: Schlessinger J. , "Cell signaling by receptor tyrosine kinases",*Cell* 103(2), p.211–225 (2000); Cobleigh, M. A., Vogel, C. L., Tripathy, D., Robert, N. J., Scholl, S., Fehrenbacher, L., Wolter, J. M., Paton, V., Shak, S., Lieberman, G., and Slamon, D. J., "Multinational study of the efficacy and safety of humanized anti-HER2 monoclonal antibody in women who have HER2-overexpressing metastatic breast cancer that has progressed after chemotherapy for metastatic disease", *J. of Clin. Oncol.* 17(9), p. 2639–2648 (1999); Baselga, J., Pfister, D., Cooper, M. R., Cohen, R., Burtness, B., Bos, M., D'Andrea, G., Seidman, A., Norton, L., Gunnett, K., Falcey, J., Anderson, V., Waksal, H., and Mendelsohn, J., "Phase I studies of anti-epidermal growth factor receptor chimeric antibody C225 alone and in combination with cisplatin", *J. Clin. Oncol.* 18(4), p. 904–914 (2000); Satoh, K., Kikuchi, S., Sekimata, M., Kabuyama, Y., Homma, M. K., and Homma Y., "Involvement of ErbB-2 in rheumatoid synovial cell growth",*Arthritis Rheum.* 44(2), p. 260–265 (2001).

The antiproliferative treatment defined herein before may be applied as a sole therapy or may involve, in addition to a compound of the invention, one or more other substances and/or treatments. Such conjoint treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

In the field of medical oncology it is normal practice to use a combination of different forms of treatment to treat each patient with cancer. In medical oncology the other component(s) of such conjoint treatment in addition to the antiproliferative treatment defined herein before may be: surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin $\alpha v \beta 3$ function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, borazole, exemestane), antihormones, antiprogestogens, antiandrogens (for example, flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as Avastin® (bevacizumab) and Erbitux® (cetuximab); tyrosine kinase inhibitors, serine/threonine kinase inhibitors and inhibitors of insulin growth receptor); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); Intercalating antitumour antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide nitrosoureas, thiotepa; antimitotic agents (for example, vinca alkaloids like vincristine, vinorelbine, vinblastine and vinflunine, and taxoids such as Taxol® (paclitaxel), Taxotere® (docetaxel) and newer microbtubule agents such as epothilone analogs, discodermolide analogs, and eleutherobin analogs); topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as Velcade® (bortezomib).

As stated above, the formula I compounds of the present invention are of interest for their antiproliferative effects. Such compounds of the invention are expected to be useful in a wide range of disease states including cancer, psoriasis, and rheumatoid arthritis.

More specifically, the compounds of formula I are useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, and osteosarcoma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, pulmonary fibrosis, arthritis, psoriasis, glomerulonephritis, restenosis following angioplasty or vascular surgery, hypertrophic scar formation and inflammatory bowel disease The compounds of formula I are especially useful in treatment of tumors having a high incidence of tyrosine kinase activity, such as colon, lung, and pancreatic tumors. By the administration of a composition (or a combination) of the compounds of this invention, development of tumors in a mammalian host is reduced.

Compounds of formula I may also be useful in the treatment of diseases other than cancer that may be associated with signal transduction pathways operating through growth factor receptors such as HER1 (EGF receptor), HER2, or HER4.

The pharmaceutical compositions of the present invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropyl-cellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS.TM. model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent (s).

The compounds may be administered in a dosage range of about 0.05 to 200 mg/kg/day, preferably less than 100 mg/kg/day, in a single dose or in 2 to 4 divided doses.

Biological Assays

HER1, HER2 or HER4 Kinase Assays

Compounds of interest were assayed in a kinase buffer that contained 20 mM Tris.HCl, pH 7.5, 10 mM $MnCl_2$, 0.5 mM dithiothreitol, bovine serum albumin at 0.1 mg/ml, poly(glu/tyr, 4:1) at 0.1 mg/ml, 1 $\mu$M ATP, and 4 $\mu$Ci/ml [$\gamma$-$^{33}$P]ATP. Poly(glu/tyr, 4:1) is a synthetic polymer that serves as a phosphoryl acceptor and is purchased from Sigma Chemicals. The kinase reaction is initiated by the addition of enzyme and the reaction mixtures were incubated at 26° C. for 1 h. The reaction is terminated by the addition of EDTA to 50 mM and proteins are precipitated by the addition of trichloroacetic acid to 5%. The precipitated proteins are recovered by filtration onto Packard Unifilter plates and the amount of radioactivity incorporated is measured in a Topcount scintillation counter.

For the preparation of recombinant HER1 and HER4, the cytoplasmic sequences of the receptors were expressed in insect cells as GST fusion proteins, which were purified by affinity chromatography. The cytoplasmic sequence of HER2 was subcloned into the baculovirus expression vector pBlueBac4 (Invitrogen) and was expressed as an untagged protein in insect cells. The recombinant protein was partially purified by ion-exchange chromatography.

The instant compounds inhibit HER1, HER2, and HER4 kinases with $IC_{50}$ values between 0.001 and 25 $\mu$M. Preferred compounds have $IC_{50}$ values between 0.001–5.0 $\mu$M. More preferred compounds have $IC_{50}$ values between 0.001–1.0 $\mu$M. Most preferred compounds have $IC_{50}$ values between 0.001–0.1 $\mu$M.

A HERG potassium channel assay may be used to screen compounds for HERG activity (see Caballero R, et al., *Direct Effects of Candesartan and Eprosartan on Human Cloned Potassium Channels Involved in Cardiac Repolarization*, Molecular Pharmacology, Vol. 59, No. 4, pp. 825–36, 2001). Accordingly, preferred compounds have lower HERG assay activity.

Methods of Preparation

Certain compounds of formula I may generally be prepared according to the following schemes and the knowledge of one skilled in the art. Supplemental preparation information may also be found in co-pending U.S. patent application Ser. No. 09/573,829 filed May 18, 2000 and international application published under the Patent Cooperation Treaty (PCT), International Publication Number WO 00/71129, both herein incorporated by reference.

Scheme 1

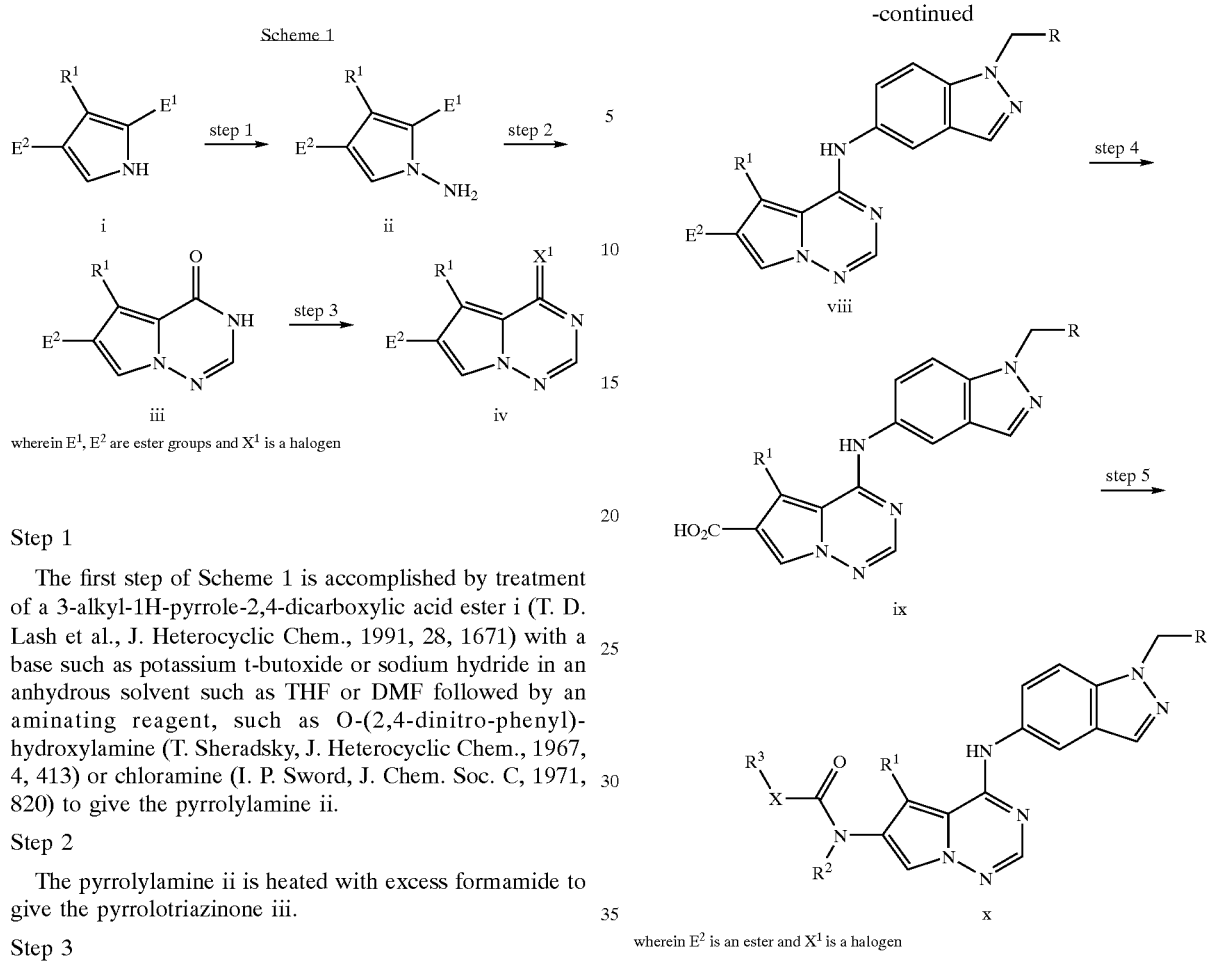

wherein E¹, E² are ester groups and X¹ is a halogen

Step 1

The first step of Scheme 1 is accomplished by treatment of a 3-alkyl-1H-pyrrole-2,4-dicarboxylic acid ester i (T. D. Lash et al., J. Heterocyclic Chem., 1991, 28, 1671) with a base such as potassium t-butoxide or sodium hydride in an anhydrous solvent such as THF or DMF followed by an aminating reagent, such as O-(2,4-dinitro-phenyl)-hydroxylamine (T. Sheradsky, J. Heterocyclic Chem., 1967, 4, 413) or chloramine (I. P. Sword, J. Chem. Soc. C, 1971, 820) to give the pyrrolylamine ii.

Step 2

The pyrrolylamine ii is heated with excess formamide to give the pyrrolotriazinone iii.

Step 3

Compound iii is converted to a 4-halo-pyrrolotriazine iv by heating with the appropriate phosphorus oxyhalide, e.g., the 4-chloro-pyrrolotriazine is obtained by heating iii with phosphorus oxychloride. The 4-halo-pyrrolotriazine iv can be converted into compound x as outlined in Scheme 2.

Scheme 2

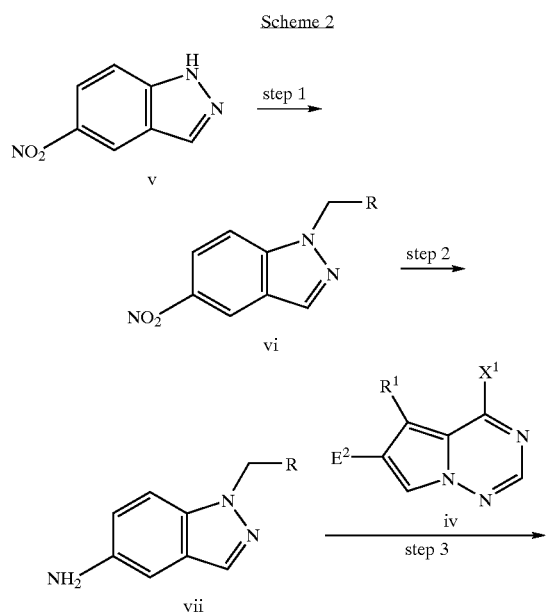

wherein E² is an ester and X¹ is a halogen

Step 1
5-Nitroindazole v can be alkylated to give indazole vi. This can be accomplished under a variety of conditions, for example, by heating a mixture of v, potassium carbonate, and the appropriate alkylating agent in DMF.

Step 2
The nitroindazole vi is reduced to the corresponding aminoindazole vii under standard conditions, such as, hydrogenation of vi over 5% platinum on carbon in ethanol.

Step 3
Treatment of 5-amino-indazole derivative vii with the 4-halo-pyrrolotriazine iv at room temperature in the presence of a base such as $NaHCO_3$ or triethylamine in a solvent such as acetonitrile gives the coupled product viii. Heating vi with a 5-amino-indazole derivative in the absence of base may also afford viii.

Step 4
The carboxylic acid ester viii can be saponified by treatment with a base such as an aqueous solution of LiOH and then acidified by treatment with an acid such as HCl to give the carboxylic acid ix.

Step 5
Conversion of the carboxylic acid ix to the final product x can be accomplished under a variety of conditions. For example, the carboxylic acid ix can be converted to the corresponding isocyanate via Curtius rearrangement by treatment with an appropriate azide such as diphenylphosphorazidate in the presence of a base such as triethylamine. The intermediate isocyanate is then trapped with the appropriate nucleophile such as an alcohol or amine to give the corresponding urea or urethane x.

In addition, other compounds of formula I may be prepared using procedures generally known to those skilled in the art. In particular, the following examples provide additional methods for the preparation of the compounds of this invention.

EXAMPLES

The invention will now be further described by the following working examples(s), which are preferred embodiments of the invention. All temperatures are in degrees Celsius (° C.) unless otherwise indicated. "HPLC Ret Time (Rt)" is the HPLC retention time that was obtained under the following conditions: Hypersil C18 BDS column, 250×4.6 mm, 5 μm, a detection wavelength of 254 nm, and a flow rate of 1 mL/min. A linear gradient of 90% of 0.1% trifluoroacetic acid in water, 10% acetonitrile (start) to 100% acetonitrile over 15 min, then 100% acetonitrile for 5 min was used. For YMC column HPLC, all gradients started with 100% solvent A (10% MeOH, 90% $H_2O$, 0.1% TFA) and ended with 100% solvent B (90% MeOH, 10% $H_2O$, 0.1% TFA)], flow rate (mL/min). UV detection was always conducted at 220 nM.

$^1$H NMR spectra were recorded at room temperature on a Bruker 300 M Hz spectrometer in $CDCl_3$ unless otherwise stated, and tetramethylsilane was used as an internal standard. Optical rotations were determined using a Perkin Elmer polarimeter. Melting points were determined on a Barnstead Thermolyne MelTemp II melting point apparatus and are uncorrected.

These examples are illustrative rather than limiting and it is to be understood that there may be other embodiments that fall within the spirit and scope of the invention as defined by the claims appended hereto.

Example 1

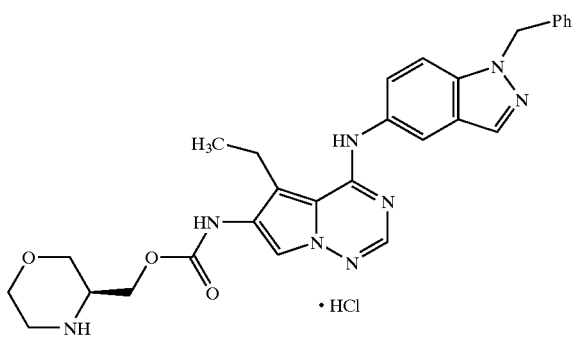

[5-ethyl-4-[[(1-phenylmethyl)-1H-indazol-5-yl]amino]pyrrolo[2,1-f][1,2,4]triazin-6-yl]-carbamic acid, (3S)-3-morpholinylmethyl ester A. 1-Benzyl-5-Nitroindazole.

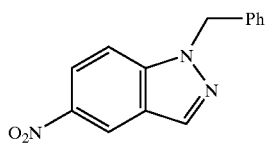

A 12 L 3-necked round-bottomed flask was charged with DMF (2 L), 5-nitroindazole (200 g, 1.22 mol.) and potassium carbonate (186 g, 1.35 mol). Benzyl bromide (230 g, 1.35 mol) was then added to the stirred suspension at a rate as to maintain the temperature below 40° C. Once the addition was complete the mixture was heated to 75° C. for a further 8 hours, the reaction being monitored by TLC ($SiO_2$, 1:1 ethyl acetate:hexanes). The reaction was then cooled to room temperature, water (2 L) added and the resulting slurry stirred at room temperature for 0.5 h. The resulting yellow solids were filtered off and dried at 45° C. and 5 mm Hg vacuum for 48 h. This afforded 424 g of a 1.25:1 mixture of 1- and 2-benzyl-5-nitroindazoles as determined by HPLC analysis ($R_t$ 1-benzyl=14.9 min, $R_t$ 2-benzyl=14.1 min). This material was then split into four approximately 100 g batches and each batch dissolved in acetone (470 mL). Water (156 mL) was then added slowly as a steady stream. After stirring for an additional 1 hour at room temperature the resulting solids were filtered off and vacuum dried. This process afforded a combined total of 126 g (41%) of 1-benzyl-5-nitroindazole, which was 92.1% pure by HPLC analysis, the major contaminant being the 2-benzyl derivative.

$^1$H NMR: δ=8.72 (d, J=2.0 Hz, 1H), 8.24 (s, 1H), 8.21 (dd, J=9.2 and 2.0 Hz, 1H), 7.19–7.40 (m, 6H) and 5.64 ppm (s, 2H). HPLC: $R_t$=14.9 min.

B. 5-Amino-1-Benzylindazole

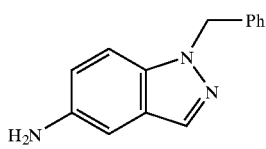

A 500 mL Parr hydrogenator bottle was charged with 1-benzyl-5-nitroindazole (30.4 g, 120 mmol), absolute ethanol (240 mL) and 5% platinum on carbon (1.5 g, 50% wet). The bottle was placed on a Parr hydrogenation apparatus, the bottle pressurized with hydrogen to 50 psi and the bottle shook until the uptake of hydrogen ceased. The contents of the bottle were then transferred to a 1L round bottomed flask, warmed to approximately 60° C. under nitrogen and rapidly filtered through a celite pad. The filter cake was washed with ethanol (100 mL). Water (250 mL) was then added to the filtrate and the resulting suspension stirred for 4 hours in an ice bath. The resulting solids were isolated by filtration, and the solids dried on the pump for 1 h. Three additional reduction runs were carried out under identical conditions. The four separate batches of material were then combined to give 87.4 g of crude material, which was re-crystallized from ethyl acetate (900 mL). Filtration and drying under reduced pressure (1 mmHg) afforded 65.0 g (59%) of the title compound as a light yellow solid.

Mpt=148–149° C. $^1$H NMR: δ 7.82 (d, J=1.0 Hz, 1H), 7.12–7.28 (m, 6H), 6.93 (d, J=2.1 Hz, 1H), 6.80 (dd, J=8.8, 2.1 Hz, 1H), 5.52 (s, 2H) and 3.56 ppm (bs, 2H) HPLC: $R_t$=9.1 min. m/z=224 (M+H)$^+$.

C. Methyl 4-(1-Benzyl-1H-indazol-5-ylamino)-5-ethylpyrrolo[2,1-f][1,2,4]triazine-6-carboxylate

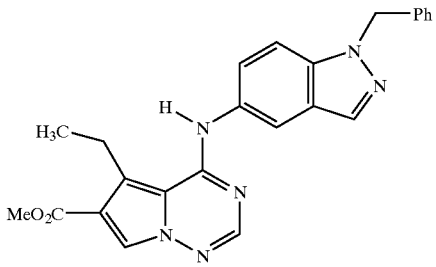

A 1 L round bottomed flask was charged with methyl 5-ethyl-4-oxo-3,4-dihydro-pyrrolo[2,1-f][1,2,4]triazine-6-carboxylate (25.0 g, 113 mmol), toluene (375 mL) and diisopropylethylamine (11.8 g, 91.6 mmol). Phosphorous oxychloride (20.7 g, 135 mmol) was then added drop-wise at room temperature (exothermic). Once the addition was complete the reaction mixture was heated to 100° C. for 20 hrs. Analysis of an aliquot by HPLC indicated that the starting material had been completely consumed ($R_t$ starting material=10.6 min, $R_t$ product=15.2 min). The reaction was then cooled and slowly poured into a mixture of saturated sodium hydrogen carbonate solution (500 mL), toluene (500 mL) and ice water (350 mL). After stirring for 30 minutes the organic layer was separated and washed with saturated sodium hydrogen carbonate solution (500 mL). Drying over sodium sulfate, filtration and concentration afforded 30.5 g (>100%) of crude methyl 4-chloro-5-ethylpyrrolo[2,1-f][1,2,4]triazine-6-carboxylate. This material was dissolved in acetonitrile (800 mL) and the solution charged to a 2 L round bottomed flask. Sodium hydrogen carbonate (15.1 g, 180 mmol) and 5-amino-1-benzylindazole (27.8 g, 124 mmol) were then added followed by additional acetonitrile (400 mL). The resulting suspension was then stirred at room temperature for 16 h. HPLC analysis after this time indicated that approximately 17% of the starting indazole remained. The mixture was then heated to reflux for 1 hr after which time only 5% of the starting indazole remained. After cooling, the mixture was concentrated and the residue partitioned between methylene chloride (800 mL) and water (300 mL). The lower organic layer was separated and washed further with water (300 mL). Drying over sodium sulfate, filtration and concentration under reduced pressure afforded 51.3 g (100%) of methyl 4-(1-benzyl-1H-indazol-5-ylamino)-5-ethylpyrrolo[2,1-f][1,2,4]triazine-6-carboxylate, which was used without further purification.

$^1$H NMR: δ=8.08 (d, J=1.5 Hz, 1H), 8.05 (d, J=0.7 Hz, 1H), 7.99 (s, 1H), 7.93 (s, 1H), 7.18–7.43 (m, 7H), 5.60 (s, 2H), 3.88, (s, 3H), 3.33 (q, J=7.1 Hz, 2H) and 1.39 ppm (t, J=7.1 Hz, 3H). HPLC $R_t$=15.0 min. m/z=427 (M+H)$^+$.

D. 4-(1-Benzyl-1H-indazol-5-ylamino)-5-ethylpyrrolo[2,1-f][1,2,4]triazine-6-carboxylic acid

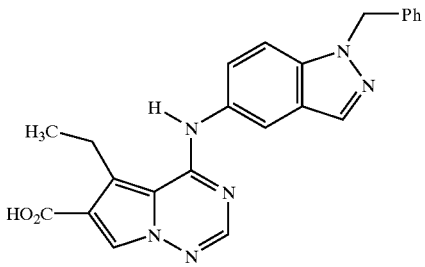

Methyl 4-(1-benzyl-1H-indazol-5-ylamino)-5-ethylpyrrolo[2,1-f][1,2,4]triazine-6-carboxylate (51.3 g, 0.12 mol) was dissolved in THF (750 mL) and the solution added to a 2 L round bottomed flask equipped with a reflux condenser. Methanol (250 mL) was then added to the flask followed by a solution of lithium hydroxide monohydrate (60.8 g, 1.45 mol) in water (300 mL). The reaction was then heated to reflux for 20 hrs. HPLC analysis of the mixture after this time indicated that the reaction was complete. The reaction was then cooled and the mixture concentrated under reduced pressure. Water (200 mL) was then added to the residue and the resulting solution extracted with ethyl acetate (2×100 mL). Hydrochloric acid (2N) was then added to the aqueous solution until a pH of 3–4 was obtained. This resulted in the formation of a thick white precipitate, which was filtered off. The filter cake was then slurried in ethyl ether (1 L), re-filtered and dried, affording 29.2 g of 4-(1-benzyl-1H-indazol-5-ylamino)-5-ethylpyrrolo[2,1-f][1,2,4]triazine-6-carboxylic acid. The filtrate was combined with the original ethyl acetate extract and the solvents removed under reduced pressure. Purification of the residue by trituration with a 2:1 mixture of ether and ethyl acetate (500 mL) followed by filtration and drying, afforded a further 13.4 g of the desired acid. The combined total yield of 4-(1-benzyl-1H-indazol-5-ylamino)-5-ethylpyrrolo[2,1-f][1,2,4]triazine-6-carboxylic acid was 42.6 g (86%) and the material had an HPLC purity of 98.2%.

Mpt=246–248° C. $^1$H NMR (DMSO-$d_6$): δ=12.47 (bs, 1H), 8.74 (s, 1H), 8.14 (s, 1H), 8.04 (s, 1H), 7.97 (d, J=1.4 Hz, 1H), 7.87 (s, 1H), 7.70 (d, J=9.0 Hz, 1H), 7.51 (dd, J=9.0 and 1.8 Hz, 1H), 7.34–7.21 (m, 5H), 5.69 (s, 2H), 3.37 (q, J=7.2 Hz, 2H) and 1.22 ppm (t, J=7.2 Hz, 3H), HPLC: $R_t$=12.2 min. m/z=413 (M+H)$^+$.

E. (S)-(+)-N-Benzylserine

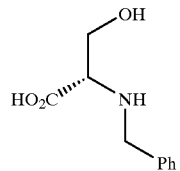

This material was prepared by the procedure reported in Brown, G. R.; Foubister, A. J.; Wright, B. *J. Chem. Soc. Perkin Trans. I*, 1985, 2577.

A 5 L 3-neck round bottom flask was charged with L-serine (313 g, 3.0 mol) and 2N sodium hydroxide solution (1.5 L). Stirring was begun and benzaldehyde (322.4 g, 3.0 mol) added. After 15 minutes at room temperature the solution was cooled to 5° C. and sodium borohydride (35.0 g, 0.93 mol) was added in small portions so as to maintain the temperature below 10° C. Once the addition was complete the solution was allowed to warm to room temperature and stir for 2 h. At this point, a second portion of benzaldehyde (322.4 g, 3.0 mol) was added and the solution stirred for 15 minutes. The solution was cooled to 5° C. and sodium borohydride (35.0 g, 0.93 mol) added, again maintaining the temperature below 10° C. The reaction mixture was then warmed to room temperature and stirred for 2 h. Diethyl ether (1 L) was added, the solution stirred 5–10 minutes and the ether layer separated. The pH of the aqueous layer was then adjusted to 6 with 37% hydrochloric acid. Filtration of the resulting solids and recrystallization of the wet cake from water afforded 230 g (40%) of (S)-(+)-N-benzylserine after drying at 45° C. overnight.

$[α]_{25}^D$+4.8° (c=1.0, 6M HCl). Mpt=218–226° C. $^1$H NMR (D$_2$O): δ=7.54 (s, 5H), 4.34 (d, J=5.5 Hz, 2H), 4.02 (q, J=3.0 Hz, 2H), and 3.75 ppm (t, J=4.4 Hz, 1H).

F. Preparation of (S)-(+)-4-Benzylmorpholin-5-one-3-carboxylic acid

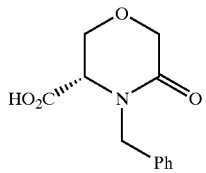

This material was prepared by the procedure reported in Brown, G. R.; Foubister, A. J.; Wright, B. *J. Chem. Soc. Perkin Trans. I*, 1985, 2577.

A 5 L 3-neck round bottom flask was charged with (S)-(+)-N-benzylserine (229 g, 1.17 mol), sodium hydroxide (58.7 g, 1.47 mol), and water (1 L). The resulting solution was cooled to 0° C. and chloroacetyl chloride (170.4 g, 1.5 mol) added dropwise at a rate to maintain the temperature below 4° C. After addition was complete the reaction was stirred at 0° C. for 30 minutes. The cold bath was then removed and a solution of 30% sodium hydroxide (350 mL) added. An exotherm was observed and the reaction temperature reached 29° C. The reaction mixture was further heated to 33° C. and maintained at this temperature for 2 hours. Cooling to room temperature followed by acidification to pH 1 with 37% hydrochloric acid resulted in the formation of a thick white precipitate, which was isolated by filtration. The filter cake was slurried in acetonitrile (1 L), filtered, and the filtrate concentrated. Drying of the resulting solid afforded 68.1 g (25%) of (S)-(+)-4-benzylmorpholin-5-one-3-carboxylic acid as a crystalline white solid.

$[\alpha]_{25}^{D}$+52.3° (c=1.2, MeOH). Mpt=173–177° C. $^1$H NMR (DMSO-d$_6$): δ=7.31 (s, 5H), 5.25 (d, J=15.3 Hz, 1H), 4.18 (m, 3H), and 3.88 ppm (m, 3H).

G. (R)-(−)-4-Benzyl-3-hydroxymethylmorpholine hydrochloride

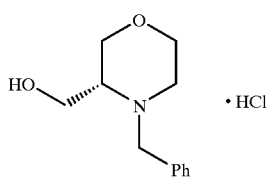

This material was prepared by the procedure reported in Brown, G. R.; Foubister, A. J.; Wright, B. *J. Chem. Soc. Perkin Trans. I*, 1985, 2577.

A 5 L 3-neck flask was charged with (S)-(+)-4-benzylmorpholin-5-one-3-carboxylic acid (102 g, 0.43 mol), triethylamine (53.3 g, 0.53 mol) and THF (1.0 L). The solution was cooled to 0° C. and a 2M solution of borane dimethyl sulfide complex in THF (1.6 L, 3.20 mol) added dropwise to the reaction flask. The reaction initially exothermed to 12° C. and rapid effervescence was observed. Once approximately 300 mL of the solution had been added, the temperature stabilized at 6° C. and effervescence ceased. The remaining solution was added over 1.5 h, maintaining the temperature at 5–6° C. The solution was then warmed to room temperature and brought to reflux. After 6 hours at reflux the reaction was cooled to room temperature and then placed in an ice/salt bath. Water (600 mL) was added drop-wise at a rate as to maintain the temperature below 10° C. Again rapid effervescence was observed. The reaction solution was then concentrated and a 2N solution of sodium hydroxide (1 L) added. Extraction with ethyl acetate (3×1 L), drying over MgSO$_4$, filtration and concentration gave a yellow oil. This oil was taken up in ethanol (2 L) and 37% hydrochloric acid (200 mL) slowly added. The addition of acid resulted in an exotherm to 45° C. and rapid effervescence was observed. After sitting for approximately 10 minutes, a white precipitate began to form. The mixture was cooled at 4° C. for 3 h and the solids filtered. The filter cake was washed with ethanol (50 mL) then dried under vacuum overnight. This afforded 78.7 g (76%) of (R)-(−)-4-benzyl-3-hydroxymethylmorpholine hydrochloride, which was used without further purification.

$[\alpha]_{25}^{D}$−14.0° (c=0.15, MeOH). Mpt=228–230° C. $^1$H NMR (CD$_3$OD): δ=7.52 (m, 5H), 4.85 (d, J=13.0 Hz 1H), 4.21 (m, 2H), 4.00 (m, 2H), 3.66–3.88 (m, 3H), 3.46 (m, 1H) and 3.20 ppm (m, 2H).

H. Preparation of (R)-(−)-3-Hydroxymethylmorpholine-4-carboxylic acid tert-Butyl ester

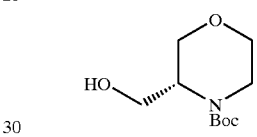

(S)-(−)-4-Benzyl-3-hydroxymethylmorpholine hydrochloride (35.0 g, 0.144 mol) was added to a mixture of ethyl acetate (250 mL) and 2N sodium hydroxide solution (200 mL) and the mixture rapidly stirred for 15 minutes. The ethyl acetate layer was then separated, dried (MgSO$_4$) and filtered. A 500 mL Parr flask was then charged with di-tert-butyl dicarbonate (32.0 g, 0.151 mol) and the above filtrate. The flask was then purged with nitrogen and palladium on carbon (1.50 g, 50% wet, 5% palladium) added. The mixture was then hydrogenated at 45 psi of hydrogen until uptake ceased (2–3 h). Filtration of the mixture through a pad of celite and concentration of the filtrate gave (R)-(−)-3-hydroxymethylmorpholine-4-carboxylic acid tert-butyl ester in quantitative yield. $^1$H NMR analysis of this material revealed the presence of approximately 5% di-tert-butyl dicarbonate. This impurity did not appear to affect subsequent chemistry and the material was used without further purification.

$[\alpha]_{25}^{D}$−56.2° (c=1.0, MeOH). Mpt=78–80° C. and 208–240° C. (two endothermic events). $^1$H NMR: δ=3.71–3.97 (m, 5H), 3.41–3.58 (m, 2H), 3.15 (m, 1H), 2.61 (t, J=5.3 Hz, 1H), and 1.47 ppm (s, 9H).

(S)-(+)-3-hydroxymethylmorpholine-4-carboxylic acid tert-butyl ester was prepared in similar fashion starting from D-serine and was obtained as a white solid.

$[\alpha]_{25}^{D}$ 58.3° (c=1.0, MeOH). Mpt=77–79° C. $^1$H NMR: δ=3.71–3.97 (m, 5H), 3.41–3.58 (m, 2H), 3.15 (m, 1H), 2.61 (t, J=5.3 Hz, 1H), and 1.47 ppm (s, 9H).

I. Preparation of 3-[[[[[5-ethyl-4-[[1-(phenylmethyl)-1H-indazol-5-yl]amino]pyrrolo[2,1-f][1,2,4]triazin-6-yl]amino]carbonyl]oxy]methyl]-4-morpholinecarboxylic acid, (3S)-1,1-dimethylethyl ester

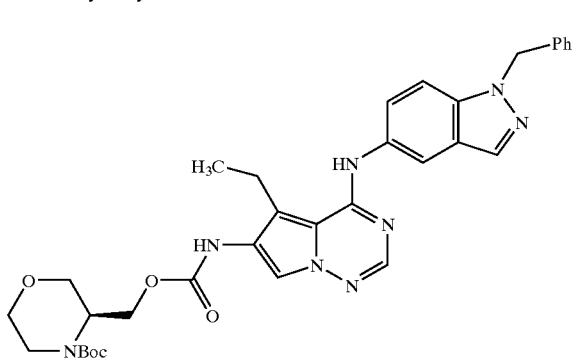

A 500 mL round bottomed flask was charged with dioxane (200 mL), 4-(1-benzyl-1H-indazol-5-ylamino)-5-ethylpyrrolo[2,1-f][1,2,4]triazine-6-carboxylic acid (14.6 g, 35.5 mmol), diphenylphosphoryl azide (12.1 g, 41.8 mmol), triethylamine (4.40 g, 43.0 mmol.) and powdered 4 Å molecular sieves (50 g) and the resulting suspension heated at 50° C. for 4 hours. The temperature was then raised to 80° C. and tert-butyl (R)-(−)-3-hydroxy-methylmorpholine-4-carboxylate (15.1 g, 67.7 mmol) added. Heating was continued for an additional 4 hours. The reaction mixture was then cooled, filtered through a celite pad and the filtrate concentrated under reduced pressure. Purification of the residue by silica gel chromatography, eluting with 1:1 hexanes/ethyl acetate, afforded 14.0 g (63%) of 3-[[[[5-ethyl-4-[[1-(phenylmethyl)-1H-indazol-5-yl]amino]pyrrolo[2,1-f][1,2,4]triazin-6-yl]amino]carbonyl]oxy]methyl]-4-morpholinecarboxylic acid, (3S)-1,1-dimethylethyl ester as a white solid.

HPLC: R$_t$=13.8 min. $^1$H NMR: δ=8.05 (s, 2H), 7.92 (s, 1H), 7.06–7.47 (m, 8H), 6.41 (bs, 1H), 5.60 (s, 2H), 4.39 (m, 3H), 3.85 (m, 3H), 3.60 (m, 1H), 3.48 (m, 1H), 3.23 (m, 1H), 2.84 (q, J=7.7 Hz, 2H), 1.44 (s, 9H), and 1.36 ppm (t, J=7.6 Hz, 3H).

J. Preparation of [5-ethyl-4-[[(1-phenylmethyl)-1H-indazol-5-yl]amino]pyrrolo[2,1-f][1,2,4]triazin-6-yl]-carbamic acid, (3S)-3-morpholinylmethyl ester, monohydrochloride

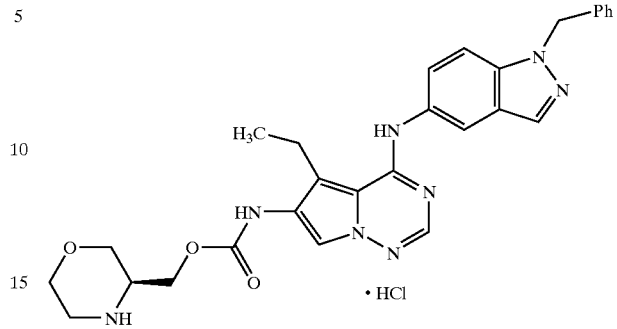

3-[[[[[5-ethyl-4-[[1-(phenylmethyl)-1H-indazol-5-yl]amino]pyrrolo[2,1-f][1,2,4]triazin-6-yl]amino]carbonyl]oxy]methyl]-4-morpholinecarboxylic acid, (3S)-1,1-dimethylethyl ester (14.0 g, 22.3 mmol) was dissolved in methylene chloride (250 mL) and treated with trifluoroacetic acid (40 mL). The resulting solution was stirred for 18 h, then neutralized by the addition of saturated aqueous sodium carbonate. The organic phase was separated and dried over magnesium sulfate. Filtration and concentration of the filtrate gave 11.4 g of [5-ethyl-4-[[(1-phenylmethyl)-1H-indazol-5-yl]amino]pyrrolo[2,1-f][1,2,4]triazin-6-yl]-carbamic acid, (3S)-3-morpholinylmethyl ester as a yellow oil. This material was re-dissolved in methylene chloride (100 mL) and treated with 1M hydrochloric acid in ether (21.7 mL, 21.7 mmol). The solution was stirred for 30 min then concentrated under reduced pressure. Drying of the residue under high vacuum (0.5 mmHg) overnight afforded 11.6 g (92%) of [5-ethyl-4-[[(1-phenylmethyl)-1H-indazol-5-yl]amino]pyrrolo[2,1-f][1,2,4]triazin-6-yl]-carbamic acid, (3S)-3-morpholinylmethyl ester hydrochloride as an off-white solid.

$[α]_{25}^D$+6.7° (c=0.1, MeOH). Mpt=>300° C. HPLC: Rt=9.95 min. $^1$H NMR (DMSO-d$_6$): δ=9.9 (bs, 2H), 9.47 (bs, 1H), 8.84 (bs, 1H), 8.15 (s, 1H), 7.49–7.98 (m, 4H), 7.34 (d, J=2.1 Hz, 1H), 7.23–7.31 (m, 5H), 5.69 (s, 2H), 4.33 (d, J=5.2 Hz, 2H), 3.60–4.03 (m, 5H), 3.10–3.29 (m, 4H), and 1.16 ppm (t, J=7.3 Hz, 3H). m/z=527 (M+H)$^+$.

The compounds shown in Table 1 were sythesized using the general procedure outlined for Example 1.

TABLE 1

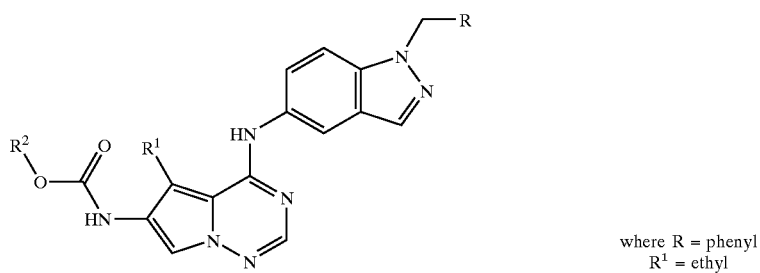

where R = phenyl
R$^1$ = ethyl

| Ex. # | R$^2$ | Compound Name | [M + H] | HPLC Ret Time (min) |
|---|---|---|---|---|
| 2 | benzyl | [4-(1-Benzyl-1H-indazol-5-ylamino)-5-ethyl-pyrrolo[2,1-f][1,2,4]triazin-6-yl]-carbamic acid benzyl ester | 518 | 1.71[1] |

TABLE 1-continued where R = phenyl
R¹ = ethyl

| Ex. # | R² | Compound Name | [M + H] | HPLC Ret Time (min) |
|---|---|---|---|---|
| 3 | imidazol-1-yl-ethyl | [4-(1-Benzyl-1H-indazol-5-ylamino)-5-ethyl-pyrrolo[2,1-f][1,2,4]triazin-6-yl]-carbamic acid 2-imidazol-1-yl-ethyl ester | 522 | 9.89 |
| 4 | 2-methyl-imidazol-1-yl-ethyl | [[4-(1-Benzyl-1H-indazol-5-ylamino)-5-ethyl-pyrrolo[2,1-f][1,2,4]triazin-6-yl]-carbamic acid 2-(2-methyl-imidazol-1-yl)-ethyl ester | 536 | 1.26[1] |
| 5 | piperidin-1-yl-ethyl | [4-(1-Benzyl-1H-indazol-5-ylamino)-5-ethyl-pyrrolo[2,1-f][1,2,4]triazin-6-yl]-carbamic acid 2-piperidin-1-yl-ethyl ester | 539 | 11.02 |
| 6 | pyridin-3-yl-(CH₂)₃ | [4-(1-Benzyl-1H-indazol-5-ylamino)-5-ethyl-pyrrolo[2,1-f][1,2,4]triazin-6-yl]-carbamic acid 3-pyridin-3-yl-propyl ester | 547 | 12.34 |
| 7 | pyridin-4-yl-(CH₂)₃ | [4-(1-Benzyl-1H-indazol-5-ylamino)-5-ethyl-pyrrolo[2,1-f][1,2,4]triazin-6-yl]-carbamic acid 3-pyridin-4-yl-propyl ester | 547 | 10.59 |
| 8 | pyridin-4-ylmethyl | [4-(1-Benzyl-1H-indazol-5-ylamino)-5-ethyl-pyrrolo[2,1-f][1,2,4]triazin-6-yl]-carbamic acid pyridin-4-ylmethyl ester | 519 | 10.32 |
| 9 | morpholin-4-yl-(CH₂)₂ | [4-(1-Benzyl-1H-indazol-5-ylamino)-5-ethyl-pyrrolo[2,1-f][1,2,4]triazin-6-yl]-carbamic acid 2-morpholin-4-yl-ethyl ester | 541 | 12.27 |
| 10 | 1-methyl-1H-imidazol-2-ylmethyl | [4-(1-Benzyl-1H-indazol-5-ylamino)-5-ethyl-pyrrolo[2,1-f][1,2,4]triazin-6-yl]-carbamic acid 1-methyl-1H-imidazol-2-ylmethyl ester | 522 | 10.10 |
| 11 | pyridin-4-yl-(CH₂)₂ | [4-(1-Benzyl-1H-indazol-5-ylamino)-5-ethyl-pyrrolo[2,1-f][1,2,4]triazin-6-yl]-carbamic acid 2-pyridin-4-yl-ethyl ester | 533 | 9.90 |

TABLE 1-continued where R = phenyl
R¹ = ethyl

| Ex. # | R² | Compound Name | [M + H] | HPLC Ret Time (min) |
|---|---|---|---|---|
| 12 | Me—N(piperazine)N—(CH₂)₂— | [4-(1-Benzyl-1H-indazol-5-ylamino)-5-ethyl-pyrrolo[2,1-f][1,2,4]triazin-6-yl]-carbamic acid 2-(4-methyl-piperazin-1-yl)-ethyl ester | 554 | 9.54 |
| 13 | pyridin-3-yl-(CH₂)₂— | [4-(1-Benzyl-1H-indazol-5-ylamino)-5-ethyl-pyrrolo[2,1-f][1,2,4]triazin-6-yl]-carbamic acid 2-pyridin-3-yl-ethyl ester | 533 | 10.33 |
| 14 | Me—N(piperidinyl)—(CH₂)₂— | [4-(1-Benzyl-1H-indazol-5-ylamino)-5-ethyl-pyrrolo[2,1-f][1,2,4]triazin-6-yl]-carbamic acid 2-(1-methyl-piperidin-4-yl)-ethyl ester | 553 | 10.57 |
| 15 | 2-methyl-imidazol-1-yl-(CH₂)₃— | [4-(1-Benzyl-1H-indazol-5-ylamino)-5-ethyl-pyrrolo[2,1-f][1,2,4]triazin-6-yl]-carbamic acid 3-(2-methyl-imidazol-1-yl)-propyl ester | 550 | 10.41 |
| 16 | 1-methyl-piperidin-4-ylmethyl— | [4-(1-Benzyl-1H-indazol-5-ylamino)-5-ethyl-pyrrolo[2,1-f][1,2,4]triazin-6-yl]-carbamic acid 1-methyl-piperidin-4-ylmethyl ester | 539 | 10.21 |
| 17 | Me—N(piperazine)N—(CH₂)₃— | [4-(1-Benzyl-1H-indazol-5-ylamino)-5-ethyl-pyrrolo[2,1-f][1,2,4]triazin-6-yl]-carbamic acid 3-(4-methyl-piperazin-1-yl)-propyl ester | 568 | 9.53 |
| 18 | i-Pr₂N—(CH₂)₂— | [4-(1-Benzyl-1H-indazol-5-ylamino)-5-ethyl-pyrrolo[2,1-f][1,2,4]triazin-6-yl]-carbamic acid 2-diisopropylamino-ethyl ester | 555 | 10.77 |
| 19 | piperidin-1-yl-(CH₂)₃— | [4-(1-Benzyl-1H-indazol-5-ylamino)-5-ethyl-pyrrolo[2,1-f][1,2,4]triazin-6-yl]-carbamic acid 3-piperidin-1-yl-propyl ester | 553 | 10.55 |
| 20 | Me₂N—(CH₂)₂— | [4-(1-Benzyl-1H-indazol-5-ylamino)-5-ethyl-pyrrolo[2,1-f][1,2,4]triazin-6-yl]-carbamic acid 2-dimethylamino-ethyl ester | 499 | 9.97 |

TABLE 1-continued where R = phenyl
R¹ = ethyl

| Ex. # | R² | Compound Name | [M + H] | HPLC Ret Time (min) |
|---|---|---|---|---|
| 21 | Me₂N~~~(propyl)~~~ | [4-(1-Benzyl-1H-indazol-5-ylamino)-5-ethyl-pyrrolo[2,1-f][1,2,4]triazin-6-yl]-carbamic acid 3-dimethylamino-propyl ester | 513 | 10.10 |
| 22 | 1-(2,2,2-trifluoroacetyl)-piperidin-4-yl-(CH₂)₂- | [4-(1-Benzyl-1H-indazol-5-ylamino)-5-ethyl-pyrrolo[2,1-f][1,2,4]triazin-6-yl]-carbamic acid 2-[1-(2,2,2-trifluoro-acetyl)-piperidin-4-yl]-ethyl ester | 635 | 14.53 |
| 23 | piperidin-4-yl-(CH₂)₂- | [4-(1-Benzyl-1H-indazol-5-ylamino)-5-ethyl-pyrrolo[2,1-f][1,2,4]triazin-6-yl]-carbamic acid 2-piperidin-4-yl-ethyl ester | 539 | 10.43 |
| 24 | piperazin-1-yl-(CH₂)₂- | [4-(1-Benzyl-1H-indazol-5-ylamino)-5-ethyl-pyrrolo[2,1-f][1,2,4]triazin-6-yl]-carbamic acid 2-piperazin-1-yl-ethyl ester | 540 | 9.37 |
| 25 | piperazin-1-yl-(CH₂)₃- | [4-(1-Benzyl-1H-indazol-5-ylamino)-5-ethyl-pyrrolo[2,1-f][1,2,4]triazin-6-yl]-carbamic acid 3-piperazin-1-yl-propyl ester | 554 | 9.51 |
| 26 | pyrrolidin-1-yl-(CH₂)₂- | [4-(1-Benzyl-1H-indazol-5-ylamino)-5-ethyl-pyrrolo[2,1-f][1,2,4]triazin-6-yl]-carbamic acid 2-pyrrolidin-1-yl-ethyl ester | 525 | 10.34 |
| 27 | [1,2,3]triazol-1-yl-(CH₂)₂- | [4-(1-Benzyl-1H-indazol-5-ylamino)-5-ethyl-pyrrolo[2,1-f][1,2,4]triazin-6-yl]-carbamic acid 2-[1,2,3]triazol-1-yl-ethyl ester | 523 | 11.07 |
| 28 | [1,2,3]triazol-1-yl-(CH₂)₃- | [4-(1-Benzyl-1H-indazol-5-ylamino)-5-ethyl-pyrrolo[2,1-f][1,2,4]triazin-6-yl]-carbamic acid 3-[1,2,3]triazol-1-yl-propyl ester | 537 | 11.27 |

TABLE 1-continued

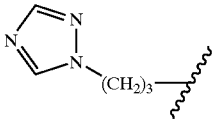

where R = phenyl
R¹ = ethyl

| Ex. # | R² | Compound Name | [M + H] | HPLC Ret Time (min) |
|---|---|---|---|---|
| 29 | 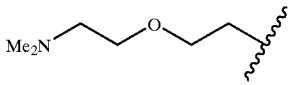 | [4-(1-Benzyl-1H-indazol-5-ylamino)-5-ethyl-pyrrolo[2,1-f][1,2,4]triazin-6-yl]-carbamic acid 3-[1,2,4]triazol-1-yl-propyl ester | 537 | 10.78 |
| 30 | 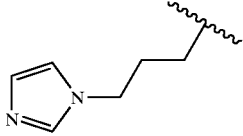 | [4-(1-Benzyl-1H-indazol-5-ylamino)-5-ethyl-pyrrolo[2,1-f][1,2,4]triazin-6-yl]-carbamic acid 2-(dimethylamino-ethoxy)-ethyl ester | 544 | 9.89 |
| 31 | 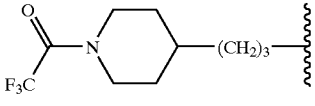 | [4-(1-Benzyl-1H-indazol-5-ylamino)-5-ethyl-pyrrolo[2,1-f][1,2,4]triazin-6-yl]-carbamic acid 3-imidazol-1-yl-propyl ester | 536 | 10.19 |
| 32 | 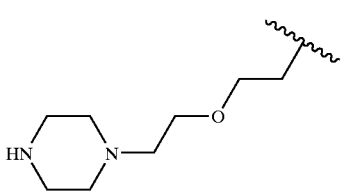 | [4-(1-Benzyl-1H-indazol-5-ylamino)-5-ethyl-pyrrolo[2,1-f][1,2,4]triazin-6-yl]-carbamic acid 3-[1-(2,2,2-trifluoro-acetyl)-piperidin-4-yl]-propyl ester | 649 | 14.90 |
| 33 | 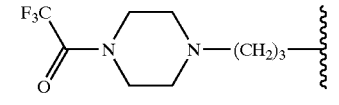 | [4-(1-Benzyl-1H-indazol-5-ylamino)-5-ethyl-pyrrolo[2,1-f][1,2,4]triazin-6-yl]-carbamic acid 2-(2-piperazin-1-yl-ethoxy)-ethyl ester | 584 | 9.48 |
| 34 | 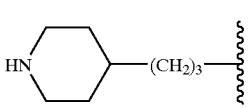 | [4-(1-Benzyl-1H-indazol-5-ylamino)-5-ethyl-pyrrolo[2,1-f][1,2,4]triazin-6-yl]-carbamic acid 3-[4-(2,2,2-trifluoro-acetyl)-piperazin-1-yl]-propyl ester | 650 | 11.03 |
| 35 | 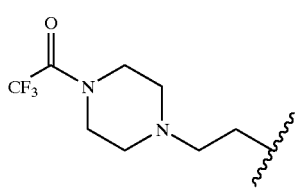 | [4-(1-Benzyl-1H-indazol-5-ylamino)-5-ethyl-pyrrolo[2,1-f][1,2,4]triazin-6-yl]-carbamic acid 3-piperidin-4-yl-propyl ester | 553 | 10.70 |
| 36 |  | [4-(1-Benzyl-1H-indazol-5-ylamino)-5-ethyl-pyrrolo[2,1-f][1,2,4]triazin-6-yl]-carbamic acid 2-[4-(2,2,2-trifluoro-acetyl)-piperazin-1-yl]-ethyl ester | 636 | 11.13 |

TABLE 1-continued where R = phenyl
R¹ = ethyl

| Ex. # | R² | Compound Name | [M + H] | HPLC Ret Time (min) |
|---|---|---|---|---|
| 37 | piperidin-4-ylmethyl | [4-(1-Benzyl-1H-indazol-5-ylamino)-5-ethyl-pyrrolo[2,1-f][1,2,4]triazin-6-yl]-carbamic acid piperidin-4-ylmethyl ester | 525 | 10.21 |
| 38 | 2-piperidin-1-yl-ethyl | [4-(1-Benzyl-1H-indazol-5-ylamino)-5-ethyl-pyrrolo[2,1-f][1,2,4]triazin-6-yl]-carbamic acid 2-piperidin-1-yl-ethyl ester | 538 | 9.84 |
| 39 | 2-[1,2,4]triazol-1-yl-ethyl | [4-(1-Benzyl-1H-indazol-5-ylamino)-5-ethyl-pyrrolo[2,1-f][1,2,4]triazin-6-yl]-carbamic acid 2-[1,2,4]triazol-1-yl-ethyl ester | 523 | 10.58 |
| 40 | 2-pyrazol-1-yl-ethyl | [4-(1-Benzyl-1H-indazol-5-ylamino)-5-ethyl-pyrrolo[2,1-f][1,2,4]triazin-6-yl]-carbamic acid 2-pyrazol-1-yl-ethyl ester | 522 | 11.76 |
| 41 | H₂N-CH₂CH₂-O-CH₂CH₂- | [4-(1-Benzyl-1H-indazol-5-ylamino)-5-ethyl-pyrrolo[2,1-f][1,2,4]triazin-6-yl]-carbamic acid 2-(2-amino-ethoxy)-ethyl ester | 515 | 9.88 |
| 42 | H₃C-O-CH₂CH₂-O-CH₂CH₂- | [4-(1-Benzyl-1H-indazol-5-ylamino)-5-ethyl-pyrrolo[2,1-f][1,2,4]triazin-6-yl]-carbamic acid 2-(2-methoxy-ethoxy)-ethyl ester | 530 | 11.67 |
| 43 | pyrazol-1-yl-(CH₂)₃- | [4-(1-Benzyl-1H-indazol-5-ylamino)-5-ethyl-pyrrolo[2,1-f][1,2,4]triazin-6-yl]-carbamic acid 3-pyrazol-1-yl-propyl ester | 536 | 12.24 |
| 44 | MeO-CH₂CH₂-N(Me)-CH₂CH₂- | [4-(1-Benzyl-1H-indazol-5-ylamino)-5-ethyl-pyrrolo[2,1-f][1,2,4]triazin-6-yl]-carbamic acid 2-[(2-methoxy-ethyl)-methyl-amino]-ethyl ester | 543 | 10.21 |

TABLE 1-continued where R = phenyl
R¹ = ethyl

| Ex. # | R² | Compound Name | [M + H] | HPLC Ret Time (min) |
|---|---|---|---|---|
| 45 | (3-morpholin-4-yl-propyl) | [4-(1-Benzyl-1H-indazol-5-ylamino)-5-ethyl-pyrrolo[2,1-f][1,2,4]triazin-6-yl]-carbamic acid 3-morpholin-4-yl-propyl ester | 555 | 10.12 |
| 46 | (2-(4-isocyanomethyl-piperazin-1-yl)-ethyl) | [4-(1-Benzyl-1H-indazol-5-ylamino)-5-ethyl-pyrrolo[2,1-f][1,2,4]triazin-6-yl]-carbamic acid 2-(4-isocyanomethyl-piperazin-1-yl)-ethyl ester | 579 | 1.17³ |
| 47 | (2-[(2-cyano-ethyl)-methyl-amino]-ethyl) | [4-(1-Benzyl-1H-indazol-5-ylamino)-5-ethyl-pyrrolo[2,1-f][1,2,4]triazin-6-yl]-carbamic acid 2-[(2-cyano-ethyl)-methyl-amino]-ethyl ester | 538 | 10.50 |
| 48 | (1-(2-methoxy-ethyl)-piperidin-4-ylmethyl) | [4-(1-Benzyl-1H-indazol-5-ylamino)-5-ethyl-pyrrolo[2,1-f][1,2,4]triazin-6-yl]-carbamic acid 1-(2-methoxy-ethyl)-piperidin-4-ylmethyl ester | 583 | 10.73 |
| 49 | (2-[1-(2-methoxy-ethyl)-piperidin-4-yl]-ethyl) | [4-(1-Benzyl-1H-indazol-5-ylamino)-5-ethyl-pyrrolo[2,1-f][1,2,4]triazin-6-yl]-carbamic acid 2-[1-(2-methoxy-ethyl)--ethyl ester | 597 | 10.99 |
| 50 | (2-[(2-fluoro-ethyl)-methyl-amino]-ethyl) | [4-(1-Benzyl-1H-indazol-5-ylamino)-5-ethyl-pyrrolo[2,1-f][1,2,4]triazin-6-yl]-carbamic acid 2-[(2-fluoro-ethyl)-methyl-amino]-ethyl ester | 531 | 10.59 |
| 51 | (3-[(2-fluoro-ethyl)-methyl-amino]-propyl) | [4-(1-Benzyl-1H-indazol-5-ylamino)-5-ethyl-pyrrolo[2,1-f][1,2,4]triazin-6-yl]-carbamic acid 3-[(2-fluoro-ethyl)-methyl-amino]-propyl ester | 545 | 10.61 |
| 52 | Me—N(piperidine)(CH₂)₃ | [4-(1-Benzyl-1H-indazol-5-ylamino)-5-ethyl-pyrrolo[2,1-f][1,2,4]triazin-6-yl]-carbamic acid 3-(1-methyl-piperidin-4-yl)-propyl ester | 567 | 11.16 |

TABLE 1-continued where R = phenyl
R¹ = ethyl

| Ex. # | R² | Compound Name | [M + H] | HPLC Ret Time (min) |
|---|---|---|---|---|
| 53 | (piperazine with methanesulfonyl-ethyl) | [4-(1-Benzyl-1H-indazol-5-ylamino)-5-ethyl-pyrrolo[2,1-f][1,2,4]triazin-6-yl]-carbamic acid 2-[4-(2-methanesulfonyl-ethyl)-piperazin-1-yl]-ethyl ester | 646 | 1.15[4] |
| 54 | (piperazine with cyanoethyl) | [4-(1-Benzyl-1H-indazol-5-ylamino)-5-ethyl-pyrrolo[2,1-f][1,2,4]triazin-6-yl]-carbamic acid 2-[4-(2-cyano-ethyl)-piperazin-1-yl]-ethyl ester | 593 | 1.09[5] |
| 55 | (piperazine with methoxyethyl) | [4-(1-Benzyl-1H-indazol-5-ylamino)-5-ethyl-pyrrolo[2,1-f][1,2,4]triazin-6-yl]-carbamic acid 2-[4-(2-methoxy-ethyl)-piperazin-1-yl]-ethyl ester | 599* | 9.84 |
| 56 | (N-methyl-N-(2-methoxyethyl)aminopropyl) | [4-(1-Benzyl-1H-indazol-5-ylamino)-5-ethyl-pyrrolo[2,1-f][1,2,4]triazin-6-yl]-carbamic acid 3-[(2-methoxy-ethyl)-methyl-amino]-propyl ester | 557 | 10.52 |
| 57 | (N-methyl-N-cyanomethyl-aminopropyl) | [4-(1-Benzyl-1H-indazol-5-ylamino)-5-ethyl-pyrrolo[2,1-f][1,2,4]triazin-6-yl]-carbamic acid 3-(cyanomethyl-methyl-amino)-propyl ester | 538 | 11.02 |
| 58 | (N-methyl-N-cyanomethyl-aminoethyl) | [4-(1-Benzyl-1H-indazol-5-ylamino)-5-ethyl-pyrrolo[2,1-f][1,2,4]triazin-6-yl]-carbamic acid 2-(cyanomethyl-methyl-amino)-ethyl ester | 524 | 11.42 |
| 59 | (N-methyl-N-(2-methanesulfonyl-ethyl)-aminopropyl) | [4-(1-Benzyl-1H-indazol-5-ylamino)-5-ethyl-pyrrolo[2,1-f][1,2,4]triazin-6-yl]-carbamic acid 3-[(2-methanesulfonyl-ethyl)-methyl-amino]-propyl ester | 606* | 10.37 |
| 60 | (4,4-difluoropiperidin-1-yl-propyl) | [4-(1-Benzyl-1H-indazol-5-ylamino)-5-ethyl-pyrrolo[2,1-f][1,2,4]triazin-6-yl]-carbamic acid 3-(4,4-difluoro-piperidin-1-yl)-propyl ester | 589 | 1.25[3] |

TABLE 1-continued

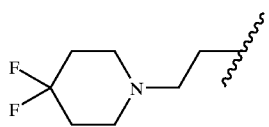

where R = phenyl
R¹ = ethyl

| Ex. # | R² | Compound Name | [M + H] | HPLC Ret Time (min) |
|---|---|---|---|---|
| 61 | 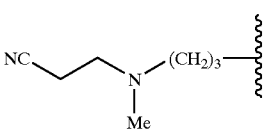 | [4-(1-Benzyl-1H-indazol-5-ylamino)-5-ethyl-pyrrolo[2,1-f][1,2,4]triazin-6-yl]-carbamic acid 2-(4,4-difluoro-piperidin-1-yl)-ethyl ester | 575 | 1.23[3] |
| 62 | 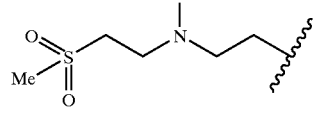 | [4-(1-Benzyl-1H-indazol-5-ylamino)-5-ethyl-pyrrolo[2,1-f][1,2,4]triazin-6-yl]-carbamic acid 3-[(2-cyano-ethyl)-methyl-amino]-propyl ester | 552 | 10.52 |
| 63 | 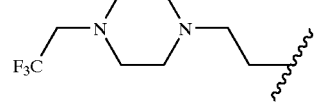 | [4-(1-Benzyl-1H-indazol-5-ylamino)-5-ethyl-pyrrolo[2,1-f][1,2,4]triazin-6-yl]-carbamic acid 2-[(2-methanesulfonyl-ethyl)-methyl-amino]-ethyl ester | 591 | 10.25 |
| 64 | 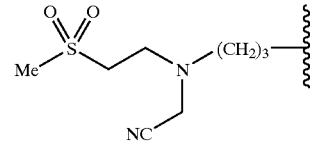 | [4-(1-Benzyl-1H-indazol-5-ylamino)-5-ethyl-pyrrolo[2,1-f][1,2,4]triazin-6-yl]-carbamic acid 2-[4-(2,2,2-trifluoro-ethyl)-piperazin-1-yl]-ethyl ester | 622 | 1.21[5] |
| 65 | 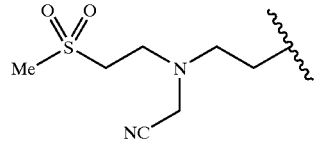 | [4-(1-Benzyl-1H-indazol-5-ylamino)-5-ethyl-pyrrolo[2,1-f][1,2,4]triazin-6-yl]-carbamic acid 3-[cyanomethyl-(2-methanesulfonyl-ethyl)-amino]-propyl ester | 6.30 | 12.32 |
| 66 | 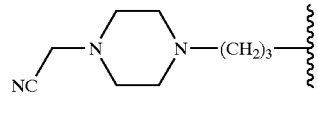 | [4-(1-Benzyl-1H-indazol-5-ylamino)-5-ethyl-pyrrolo[2,1-f][1,2,4]triazin-6-yl]-carbamic acid 2-[cyanomethyl-(2-methanesulfonyl-ethyl)-amino]-ethyl ester | 616 | 11.56 |
| 67 | 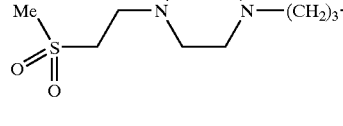 | [4-(1-Benzyl-1H-indazol-5-ylamino)-5-ethyl-pyrrolo[2,1-f][1,2,4]triazin-6-yl]-carbamic acid 3-(4-cyanomethyl-piperazin-1-yl)-propyl ester | 593 | 1.19[4] |
| 68 | | [4-(1-Benzyl-1H-indazol-5-ylamino)-5-ethyl-pyrrolo[2,1-f][1,2,4]triazin-6-yl]-carbamic acid 3-[4-(2-methanesulfonyl-ethyl)-piperazin-1-yl]-propyl ester | 660 | 10.11 |

TABLE 1-continued where R = phenyl
R¹ = ethyl

| Ex. # | R² | Compound Name | [M + H] | HPLC Ret Time (min) |
|---|---|---|---|---|
| 69 | NC-CH₂CH₂-N(piperazine)N-(CH₂)₃- | [4-(1-Benzyl-1H-indazol-5-ylamino)-5-ethyl-pyrrolo[2,1-f][1,2,4]triazin-6-yl]-carbamic acid 3-[4-(2-cyano-ethyl)-piperazin-1-yl]-propyl ester | 607 | 10.26 |
| 70 | F₃C-CH₂-N(piperazine)N-(CH₂)₃- | [4-(1-Benzyl-1H-indazol-5-ylamino)-5-ethyl-pyrrolo[2,1-f][1,2,4]triazin-6-yl]-carbamic acid 3-[4-(2,2,2-trifluoro-ethyl)-piperazin-1-yl]-propyl ester | 636 | 2.11³ |
| 71 | 1H-imidazol-2-yl-ethyl | [4-(1-Benzyl-1H-indazol-5-ylamino)-5-ethyl-pyrrolo[2,1-f][1,2,4]triazin-6-yl]-carbamic acid 2-(1H-imidazol-2-yl)-ethyl ester | 522 | 10.09 |
| 72 | Me-SO₂-CH₂CH₂-NH-CH₂CH₂- | [4-(1-Benzyl-1H-indazol-5-ylamino)-5-ethyl-pyrrolo[2,1-f][1,2,4]triazin-6-yl]-carbamic acid 2-(2-methanesulfonyl-ethylamino)-ethyl ester | 577 | 10.14 |
| 73 | NC-CH₂CH₂-N(piperidine)-CH₂- | [4-(1-Benzyl-1H-indazol-5-ylamino)-5-ethyl-pyrrolo[2,1-f][1,2,4]triazin-6-yl]-carbamic acid 1-(2-cyano-ethyl)-piperidin-4-ylmethyl ester | 578 | 1.14⁴ |
| 74 | NC-CH₂-N(piperidine)-CH₂- | [4-(1-Benzyl-1H-indazol-5-ylamino)-5-ethyl-pyrrolo[2,1-f][1,2,4]triazin-6-yl]-carbamic acid 1-cyanomethyl-piperidin-4-ylmethyl ester | 564 | 1.25⁴ |
| 75 | HO-(piperidine)N-(CH₂)₃- | [4-(1-Benzyl-1H-indazol-5-ylamino)-5-ethyl-pyrrolo[2,1-f][1,2,4]triazin-6-yl]-carbamic acid 3-(4-hydroxy-piperidin-1-yl)-propyl ester | 569 | 9.94 |
| 76 | Me-SO₂-CH₂CH₂-N(piperidine)-CH₂- | [4-(1-Benzyl-1H-indazol-5-ylamino)-5-ethyl-pyrrolo[2,1-f][1,2,4]triazin-6-yl]-carbamic acid 1-(2-methanesulfonyl-ethyl)-piperidin-4-ylmethyl ester | 631 | 1.23⁵ |
| 77 | piperidin-2-ylmethyl | [4-(1-Benzyl-1H-indazol-5-ylamino)-5-ethyl-pyrrolo[2,1-f][1,2,4]triazin-6-yl]-carbamic acid piperidin-2-ylmethyl ester | 525 | 10.37 |

TABLE 1-continued

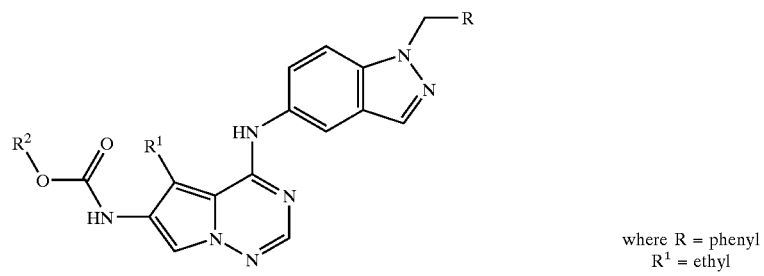

where R = phenyl
R¹ = ethyl

| Ex. # | R² | Compound Name | [M + H] | HPLC Ret Time (min) |
|---|---|---|---|---|
| 78 | | [4-(1-Benzyl-1H-indazol-5-ylamino)-5-ethyl-pyrrolo[2,1-f][1,2,4]triazin-6-yl]-carbamic acid piperidin-4-yl ester | 511 | 10.07 |
| 79 | | [4-(1-Benzyl-1H-indazol-5-ylamino)-5-ethyl-pyrrolo[2,1-f][1,2,4]triazin-6-yl]-carbamic acid 1H-imidazol-2-ylmethyl ester | 508 | 10.17 |
| 80 | | [4-(1-Benzyl-1H-indazol-5-ylamino)-5-ethyl-pyrrolo[2,1-f][1,2,4]triazin-6-yl]-carbamic acid piperidin-3-ylmethyl ester | 525 | 10.26 |
| 81 | | [4-(1-Benzyl-1H-indazol-5-ylamino)-5-ethyl-pyrrolo[2,1-f][1,2,4]triazin-6-yl]-carbamic acid 3-(1H-imidazol-2-yl)-propyl ester | 536 | 10.17 |
| 82 | | [4-(1-Benzyl-1H-indazol-5-ylamino)-5-ethyl-pyrrolo[2,1-f][1,2,4]triazin-6-yl]-carbamic acid 3-methanesulfonyl-propyl ester | 548 | 11.52 |
| 83 | | [4-(1-Benzyl-1H-indazol-5-ylamino)-5-ethyl-pyrrolo[2,1-f][1,2,4]triazin-6-yl]-carbamic acid 3-(2-methanesulfonyl-ethylamino)-propyl ester | 591 | 10.27 |
| 84 | | [5-ethyl-4-[[(1-phenylmethyl)-1H-indazol-5-yl]amino]pyrrolo[2,1-f][1,2,4]triazin-6-yl]-carbamic acid, (2R)-2-pyrrolidinylmethyl ester | 511 | 1.21³ |
| 85 | | [5-ethyl-4-[[(1-phenylmethyl)-1H-indazol-5-yl]amino]pyrrolo[2,1-f][1,2,4]triazin-6-yl]-carbainic acid, (2S)-2-pyrrolidinylmethyl ester | 511 | 1.21³ |
| 86 | | [4-(1-Benzyl-1H-indazol-5-ylamino)-5-ethyl-pyrrolo[2,1-f][1,2,4]triazin-6-yl]-carbamic acid 2-methanesulfonyl-ethyl ester | 534 | 11.33 |

TABLE 1-continued where R = phenyl
R¹ = ethyl

| Ex. # | R² | Compound Name | [M + H] | HPLC Ret Time (min) |
|---|---|---|---|---|
| 87 | NC-CH₂-NH-CH₂CH₂- | [4-(1-Benzyl-1H-indazol-5-ylamino)-5-ethyl-pyrrolo[2,1-f][1,2,4]triazin-6-yl]-carbamic acid 2-(cyanomethyl-amino)-ethyl ester | 510 | 10.19 |
| 88 | NC-CH₂-NH-(CH₂)₃- | [4-(1-Benzyl-1H-indazol-5-ylamino)-5-ethyl-pyrrolo[2,1-f][1,2,4]triazin-6-yl]-carbamic acid 3-(cyanomethyl-amino)-propyl ester | 524 | 10.27 |
| 89 | 1,1-dioxothiomorpholin-4-yl-propyl | [4-(1-Benzyl-1H-indazol-5-ylamino)-5-ethyl-pyrrolo[2,1-f][1,2,4]triazin-6-yl]-carbamic acid 3-(1,1-dioxo-1l6-thiomorpholin-4-yl)-propyl ester | 603 | 1.15[5] |
| 90 | 4-oxo-piperidin-1-yl-propyl | [4-(1-Benzyl-1H-indazol-5-ylamino)-5-ethyl-pyrrolo[2,1-f][1,2,4]triazin-6-yl]-carbamic acid 3-(4-oxo-piperidin-1-yl)-propyl ester | 567 | 1.11[4] |
| 91 | (2,2-difluoro-ethyl)-methyl-amino-ethyl | [4-(1-Benzyl-1H-indazol-5-ylamino)-5-ethyl-pyrrolo[2,1-f][1,2,4]triazin-6-yl]-carbamic acid 2-[(2,2-difluoro-ethyl)-methyl-amino]-ethyl ester | 549 | 10.44 |
| 92 | (3R)-3-morpholinylmethyl | [5-ethyl-4-[[(1-phenylmethyl)-1H-indazol-5-yl]amino]pyrrolo[2,1-f][1,2,4]triazin-6-yl]-carbamic acid, (3R)-3-morpholinylmethyl ester | 527 | 10.06 |
| 93 | 3-[(3S)-3-hydroxy-1-pyrrolidinyl]propyl | [5-ethyl-4-[[(1-phenylmethyl)-1H-indazol-5-yl]amino]pyrrolo[2,1-f][1,2,4]triazin-6-yl]-carbamic acid, 3-[(3S)-3-hydroxy-1-pyrrolidinyl]propyl ester | 555 | 1.15[4] |
| 94 | 3-[(3S)-3-hydroxy-1-piperidinyl]propyl | [5-ethyl-4-[[(1-phenylmethyl)-1H-indazol-5-yl]amino]pyrrolo[2,1-f][1,2,4]triazin-6-yl]-carbamic acid, 3-[(3S)-3-hydroxy-1-piperidinyl]propyl ester | 569 | 1.23[3] |

TABLE 1-continued where R = phenyl
R¹ = ethyl

| Ex. # | R² | Compound Name | [M + H] | HPLC Ret Time (min) |
|---|---|---|---|---|
| 95 | | [5-ethyl-4-[[(1-phenylmethyl)-1H-indazol-5-yl]amino]pyrrolo[2,1-f][1,2,4]triazin-6-yl]-carbamic acid, (3R)-3-pyrrolidinylmethyl ester | 511 | 10.15 |
| 96 | | [5-ethyl-4-[[(1-phenylmethyl)-1H-indazol-5-yl]amino]pyrrolo[2,1-f][1,2,4]triazin-6-yl]-carbamic acid, 3-[(3R)-3-hydroxy-1-pyrrolidinyl]propyl ester | 555 | 1.23[3] |
| 97 | | [4-(1-Benzyl-1H-indazol-5-ylamino)-5-ethyl-pyrrolo[2,1-f][1,2,4]triazin-6-yl]-carbamic acid 1-methyl-piperidin-4-yl ester | 525 | 10.25 |
| 98 | | [5-ethyl-4-[[(1-phenylmethyl)-1H-indazol-5-yl]amino]pyrrolo[2,1-f][1,2,4]triazin-6-yl]-carbamic acid, [(2S)-1-methyl-2-pyrrolidinyl]methyl ester | 525 | 10.31 |
| 99 | | [5-ethyl-4-[[(1-phenylmethyl)-1H-indazol-5-yl]amino]pyrrolo[2,1-f][1,2,4]triazin-6-yl]-carbamic acid, (2S)-2-morpholinylmethyl ester | 527 | 10.08 |
| 100 | | [5-ethyl-4-[[(1-phenylmethyl)-1H-indazol-5-yl]amino]pyrrolo[2,1-f][1,2,4]triazin-6-yl]-carbamic acid, (3S)-3-pyrrolidinylmethyl ester | 511 | 10.22 |
| 101 | | [4-(1-Benzyl-1H-indazol-5-ylamino)-5-ethyl-pyrrolo[2,1-f][1,2,4]triazin-6-yl]-carbamic acid 1-methyl-1,2,3,6-tetrahydro-pyridin-4-ylmethyl ester | 537 | 10.34 |
| 102 | | [5-ethyl-4-[[(1-phenylmethyl)-1H-indazol-5-yl]amino]pyrrolo[2,1-f][1,2,4]triazin-6-yl]-carbamic acid, (2R)-2-morpholinylmethyl ester | 527 | 10.13 |

TABLE 1-continued where R = phenyl
R¹ = ethyl

| Ex. # | R² | Compound Name | [M + H] | HPLC Ret Time (min) |
|---|---|---|---|---|
| 103 | NC-CH₂CH₂-N-piperidine | [4-(1-Benzyl-1H-indazol-5-ylamino)-5-ethyl-pyrrolo[2,1-f][1,2,4]triazin-6-yl]-carbamic acid 1-(2-cyano-ethyl)-piperidin-4-yl ester | 564 | 10.58 |
| 104 | HN-azetidine | [4-(1-Benzyl-1H-indazol-5-ylamino)-5-ethyl-pyrrolo[2,1-f][1,2,4]triazin-6-yl]-carbamic acid azetidin-3-yl ester | 483 | 10.01 |
| 105 | Me-SO₂-CH₂CH₂-N-piperidine | [4-(1-Benzyl-1H-indazol-5-ylamino)-5-ethyl-pyrrolo[2,1-f][1,2,4]triazin-6-yl]-carbamic acid 1-(2-methanesulfonyl-ethyl)-piperidin-4-yl ester | 617 | 10.48 |
| 106 | NC-CH₂-N-piperidine | [4-(1-Benzyl-1H-indazol-5-ylamino)-5-ethyl-pyrrolo[2,1-f][1,2,4]triazin-6-yl]-carbamic acid 1-cyanomethyl-piperidin-4-yl ester | 550 | 11.13 |
| 107 | Me₂CH-N-piperidine | [4-(1-Benzyl-1H-indazol-5-ylamino)-5-ethyl-pyrroio[2,1-f][1,2,4]triazin-6-yl]-carbamic acid 1-isopropyl-piperidin-4-yl ester | 553 | 10.71 |
| 108 | propyl-N-piperidine | [4-(1-Benzyl-1H-indazol-5-ylamino)-5-ethyl-pyrrolo[2,1-f][1,2,4]triazin-6-yl]-carbamic acid 1-propyl-piperidin-4-yl ester | 553 | 10.88 |
| 109 | MeC(O)-N-piperidine | [4-(1-Benzyl-1H-indazol-5-ylamino)-5-ethyl-pyrrolo[2,1-f][1,2,4]triazin-6-yl]-carbamic acid 1-acetyl-piperidin-4-yl ester | 553 | 11.33 |
| 110 | ethyl-N-piperidine | [4-(1-Benzyl-1H-indazol-5-ylamino)-5-ethyl-pyrrolo[2,1-f][1,2,4]triazin-6-yl]-carbamic acid 1-ethyl-piperidin-4-yl ester | 539 | 10.24 |
| 111 | allyl-N-piperidine | [4-(1-Benzyl-1H-indazol-5-ylamino)-5-ethyl-pyrrolo[2,1-f][1,2,4]triazin-6-yl]-carbamic acid 1-allyl-piperidin-4-yl ester | 551 | 10.48 |
| 112 | tetrahydropyran-4-yl | [4-(1-Benzyl-1H-indazol-5-ylamino)-5-ethyl-pyrrolo[2,1-f][1,2,4]triazin-6-yl]-carbamic acid tetrahydro-pyran-4-yl ester | 512 | 12.26 |

TABLE 1-continued

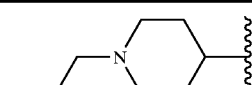

where R = phenyl
R¹ = ethyl

| Ex. # | R² | Compound Name | [M + H] | HPLC Ret Time (min) |
|---|---|---|---|---|
| 113 | 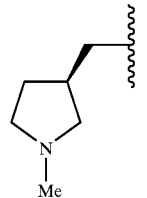 | [4-(1-Benzyl-1H-indazol-5-ylamino)-5-ethyl-pyrrolo[2,1-f][1,2,4]triazin-6-yl]-carbamic acid 1-(2-hydroxy-ethyl)-piperidin-4-yl ester | 555 | 10.17 |
| 114 | 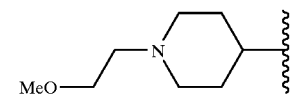 | [5-ethyl-4-[[(1-phenylmethyl)-1H-indazol-5-yl]amino]pyrrolo[2,1-f][1,2,4]triazin-6-yl]-carbamic acid, [(3R)-1-methyl-3-pyrrolidinyl]methyl ester | 525 | 10.43 |
| 115 | 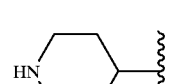 | [4-(1-Benzyl-1H-indazol-5-ylamino)-5-ethyl-pyrrolo[2,1-f][1,2,4]triazin-6-yl]-carbamic acid 1-(2-methoxy-ethyl)-piperidin-4-yl ester | 569 | 10.63 |
| 116 |  | [4-(1-Benzyl-1H-indazol-5-ylamino)-5-ethyl-pyrrolo[2,1-f][1,2,4]triazin-6-yl]-carbamic acid piperidin-4-yl ester | 497 | 9.75 |
| 117 | 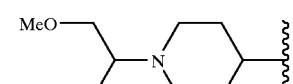 | [4-(1-Benzyl-1H-indazol-5-ylamino)-5-ethyl-pyrrolo[2,1-f][1,2,4]triazin-6-yl]-carbamic acid 1-(2-methoxy-ethyl)-azetidin-3-yl ester | 541 | 10.34 |
| 118 | 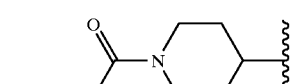 | [4-(1-Benzyl-1H-indazol-5-ylamino)-5-ethyl-pyrrolo[2,1-f][1,2,4]triazin-6-yl]-carbamic acid 1-(2-methoxy-1-methoxymethyl-ethyl)-piperidin-4-yl ester | 613 | 11.13 |
| 119 | 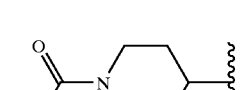 | [4-(1-Benzyl-1H-indazol-5-ylamino)-5-ethyl-pyrrolo[2,1-f][1,2,4]triazin-6-yl]-carbamic acid 1-(2-methoxy-acetyl)-piperidin-4-yl ester | 583 | 11.40 |
| 120 | 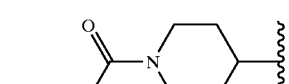 | 4-[4-(1-Benzyl-1H-indazol-5-ylamino)-5-ethyl-pyrrolo[2,1-f][1,2,4]triazin-6-f ylcarbamoyloxy]-piperidine-1-carboxylic acid methyl ester | 569 | 12.71 |
| 121 | | [4-(1-Benzyl-1H-indazol-5-ylamino)-5-ethyl-pyrrolo[2,1-f][1,2,4]triazin-6-yl]-carbamic acid 1-(2-hydroxy-acetyl)-piperidin-4-yl ester | 569 | 10.88 |

TABLE 1-continued where R = phenyl
R¹ = ethyl

| Ex. # | R² | Compound Name | [M + H] | HPLC Ret Time (min) |
|---|---|---|---|---|
| 122 | (1-acetoxy-ethyl carbamate group) | 4-[4-(1-Benzyl-1H-indazol-5-ylamino)-5-ethyl-pyrrolo[2,1-f][1,2,4]triazin-6-ylcarbamoyloxy]-piperidine-1-carboxylic acid 1-acetoxy-ethyl ester | 641 | 13.43 |
| 123 | (1-acetoxy-1-methyl-ethyl carbamate group) | 4-[4-(1-Benzyl-1H-indazol-5-ylamino)-5-ethyl-pyrrolo[2,1-f][1,2,4]triazin-6-ylcarbamoyloxy]-piperidine-1-carboxylic acid 1-acetoxy-1-methyl-ethyl ester | 655 | 13.75 |
| 124 | 1-hydroxy-piperidin-4-yl | [4-(1-Benzyl-1H-indazol-5-ylamino)-5-ethyl-pyrrolo[2,1-f][1,2,4]triazin-6-yl]-carbamic acid 1-hydroxy-piperidin-4-yl ester | 527 | 10.33 |
| 125 | trans-4-aminocyclohexyl | [5-ethyl-4-[[(1-phenylmethyl)-1H-indazol-5-yl]amino]pyrrolo[2,1-f][1,2,4]triazin-6-yl]-carbamic acid, trans-4-aminocyclohexyl ester | 525 | 10.15 |
| 126 | (3R)-3-piperidinyl | [5-ethyl-4-[[(1-phenylmethyl)-1H-indazol-5-yl]amino]pyrrolo[2,1-f][1,2,4]triazin-6-yl]-carbamic acid, (3R)-3-piperidinyl ester | 511 | 10.08 |
| 127 | (5-methyl-2-oxo-[1,3]dioxol-4-ylmethyl carbamate group) | 4-[4-(1-Benzyl-1H-indazol-5-ylamino)-5-ethyl-pyrrolo[2,1-f][1,2,4]triazin-6-ylcarbamoyloxy]-piperidine-1-carboxylic acid 5-methyl-2-oxo-[1,3]dioxol-4-ylmethyl ester | 667 | 13.36 |

TABLE 1-continued where R = phenyl
R¹ = ethyl

| Ex. # | R² | Compound Name | [M + H] | HPLC Ret Time (min) |
|---|---|---|---|---|
| 128 | (3S)-3-piperidinyl | [5-ethyl-4-[[(1-phenylmethyl)-1H-indazol-5-yl]amino]pyrrolo[2,1-f][1,2,4]triazin-6-yl]-carbamic acid, (3S)-3-piperidinyl ester | 511 | 10.13 |
| 129 | cis-4-aminocyclohexyl | [5-ethyl-4-[[(1-phenylmethyl)-1H-indazol-5-yl]amino]pyrrolo[2,1-f][1,2,4]triazin-6-yl]-carbamic acid, cis-4-aminocyclohexyl ester | 525 | 10.14 |
| 130 | (2R,4R)-2-(hydroxymethyl)-4-piperidinyl | [5-ethyl-4-[[(1-phenylmethyl)-1H-indazol-5-yl]amino]pyrrolo[2,1-f][1,2,4]triazin-6-yl]-carbamic acid, (2R,4R)-2-(hydroxymethyl)-4-piperidinyl ester | 541 | 9.89 |
| 131 | (2S)-2-(hydroxymethyl)-4-piperidinyl | [5-ethyl-4-[[(1-phenylmethyl)-1H-indazol-5-yl]amino]pyrrolo[2,1-f][1,2,4]triazin-6-yl]-carbamic acid, (2S)-2-(hydroxymethyl)-4-piperidinyl ester | 541 | 9.85 |
| 132 | cis-4-(aminomethyl)cyclohexyl | [5-ethyl-4-[[(1-phenylmethyl)-1H-indazol-5-yl]amino]pyrrolo[2,1-f][1,2,4]triazin-6-yl]-carbamic acid, cis-4-(aminomethyl)cyclohexyl ester | 539 | 10.47 |
| 133 | cis-4-amino-4-methylcyclohexyl | [5-ethyl-4-[[(1-phenylmethyl)-1H-indazol-5-yl]amino]pyrrolo[2,1-f][1,2,4]triazin-6-yl]-carbamic acid, cis-4-amino-4-methylcyclohexyl ester | 539 | 10.32 |
| 134 | [(2R,4R)-4-hydroxy-2-piperidinyl]methyl | [5-ethyl-4-[[(1-phenylmethyl)-1H-indazol-5-yl]amino]pyrrolo[2,1-f][1,2,4]triazin-6-yl]-carbamic acid, [(2R,4R)-4-(hydroxy-2-piperidinyl]methylester | 541 | 9.71 |
| 135 | trans-4-(aminomethyl)cyclohexyl | [5-ethyl-4-[[(1-phenylmethyl)-1H-indazol-5-yl]amino]pyrrolo[2,1-f][1,2,4]triazin-6-yl]-carbamic acid, trans-4-(aminomethyl)cyclohexyl ester | 539 | 10.56 |

Unless otherwise indicated, HPLC Retention Times were determined using a Hypersil BDS C18 column with a 15 minute gradient time. [1]YMC TurboPack Pro column with a 2 minute gradient. [2]YMC S5 ODS column with a 4 minute gradient. [3]YMC Xterra ODS with a 2 minute gradient. [4]YMC ODS-A C18 column with a 2 minute gradient. [5]YMC C18 S5 column with a 2 minute gradient. MS data marked with a "*" were [M+2H].

The following compounds, where R is as defined in the Table, were prepared utilizing the procedure described in Example 1.

TABLE 2

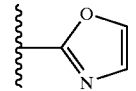

| Ex. # | R | Compound Name | M + H | HPLC Ret Time (min) |
|---|---|---|---|---|
| 136 | 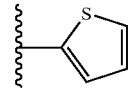 | [5-ethyl-4-[[1-(2-oxazolylmethyl)-1H-indazol-5-yl]amino]pyrrolo[2,1-f][1,2,4]triazin-6-yl]-carbamic acid, (3S)-3-morpholinylmethyl ester | 518 | 6.70 |
| 137 | 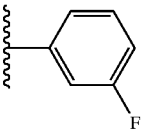 | [5-ethyl-4-[[1-(2-thienylmethyl)-1H-indazol-5-yl]amino]pyrrolo[2,1-f][1,2,4]triazin-6-yl]-carbamic acid, (3S)-3-morpholinylmethyl ester | 533 | 9.70 |
| 138 | 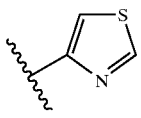 | [5-ethyl-4-[[1-[(3-fluorophenyl)methyl]-1H-indazol-5-yl]amino]pyrrolo[2,1-f][1,2,4]triazin-6-yl]-carbamic acid, (3S)-3-morpholinylmethyl ester | 545 | 10.21 |
| 139 | 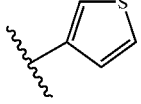 | [5-ethyl-4-[[1-(4-thiazolylmethyl)-1H-indazol-5-yl]amino]pyrrolo[2,1-f][1,2,4]triazin-6-yl]-carbamic acid, (3S)-3-morpholinylmethyl ester | 534 | 7.98 |
| 140 | 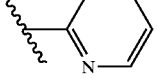 | [5-ethyl-4-[[1-(3-thienylmethyl)-1H-indazol-5-yl]amino]pyrrolo[2,1-f][1,2,4]triazin-6-yl]-carbamic acid, (3S)-3-morpholinylmethyl ester | 533 | 9.68 |
| 141 | 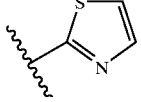 | [5-ethyl-4-[[1-(2-pyridinylmethyl)-1H-indazol-5-yl]amino]pyrrolo[2,1-f][1,2,4]triazin-6-yl]-carbamic acid, (3S)-3-morpholinylmethyl ester | 528 | 7.14 |
| 142 | 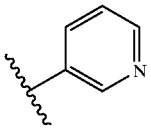 | [5-ethyl-4-[[1-(2-thiazolylmethyl)-1H-indazol-5-yl]amino]pyrrolo[2,1-f][1,2,4]triazin-6-yl]-carbamic acid, (3S)-3-morpholinylmethyl ester | 534 | 8.21 |
| 143 | | [5-ethyl-4-[[1-(3-pyridinylmethyl)-1H-indazol-5-yl]amino]pyrrolo[2,1-f][1,2,4]triazin-6-yl]-carbamic acid, (3S)-3-morpholinylmethyl ester | 528 | 6.74 |

TABLE 2-continued

| Ex. # | R | Compound Name | M + H | HPLC Ret Time (min) |
|---|---|---|---|---|
| 144 | pyrazinyl | [5-ethyl-4-[[1-(pyrazinylmethyl)-1H-indazol-5-yl]amino]pyrrolo[2,1-f][1,2,4]triazin-6-yl]-carbamic acid, (3S)-3-morpholinylmethyl ester | 529 | 7.46 |

Unless otherwise indicated, HPLC Retention Times were determined using a Hypersil BDS C18 column with a 15 minute gradient time. [1]YMC TurboPack Pro column with a 2 minute gradient. 2YMC S5 ODS column with a 4 minute gradient. [3]YMC Xterra ODS with a 2 minute gradient. [4]YMC ODS-A C18 column with a 2 minute gradient. [5]YMC C18 S5 column with a 2 minute gradient.

The following compounds, where $R^2$ is as defined in Table 3, were prepared utilizing the procedure described in Example 1 using ethyl 5-methyl-4-oxo-3,4-dihydro-pyrrolo[2,1-f][1,2,4]triazine-6-carboxylate.

TABLE 3 where R = 3-fluoro-phenyl
$R^1$ = methyl

| Ex. # | $R^2$ | Compound Name | [M + H] | Ret Time (min) |
|---|---|---|---|---|
| 145 | trans-4-aminocyclohexyl | [4-[[1-(3-fluorophenyl)methyl]-1H-indazol-5-ylamino]-5-methyl-pyrrolo[2,1-f][1,2,4]triazin-6-yl]-carbamic acid, trans-4-aminocyclohexyl ester | 529 | 10.19 |
| 146 | (2R,4R)-2-(hydroxymethyl)-4-piperidinyl | [4-[[1-(3-fluorophenyl)methyl]-1H-indazol-5-ylamino]-5-methyl-pyrrolo[2,1-f][1,2,4]triazin-6-yl]-carbamic acid, (2R,4R)-2-(hydroxymethyl)-4-piperidinyl ester | 545 | 9.84 |
| 147 | (2S,4S)-2-(hydroxymethyl)-4-piperidinyl | [4-[[1-(3-fluorophenyl)methyl]-1H-indazol-5-ylamino]-5-methyl-pyrrolo[2,1-f][1,2,4]triazin-6-yl]-carbamic acid, (2S,4S)-2-(hydroxymethyl)-4-piperidinyl ester | 545 | 9.85 |

TABLE 3-continued where R = 3-fluoro-phenyl
R¹ = methyl

| Ex. # | R² | Compound Name | [M + H] | Ret Time (min) |
|---|---|---|---|---|
| 148 | tetrahydropyran-4-yl | {4-[1-(3-Fluoro-benzyl)-1H-indazol-5-ylamino]-5-methyl-pyrrolo[2,1-f][1,2,4]triazin-6-yl}-carbamic acid tetrahydro-pyran-4-yl ester | 516 | 11.87 |
| 149 | 3-methanesulfonyl-propyl | {4-[1-(3-Fluoro-benzyl)-1H-indazol-5-ylamino]-5-methyl-pyrrolo[2,1-f][1,2,4]triazin-6-yl}-carbamic acid 3-methanesulfonyl-propyl ester | 552 | 11.19 |
| 150 | 2-amino-2-methyl-propyl | {4-[1-(3-Fluoro-benzyl)-1H-indazol-5-ylamino]-5-methyl-pyrrolo[2,1-f][1,2,4]triazin-6-yl}-carbamic acid 2-amino-2-methyl-propyl ester | 503 | 10.06 |
| 151 | cis-4-aminocyclohexyl | [4-[[1-(3-fluorophenyl)methyl]-1H-indazol-5-ylamino]-5-methyl-pyrrolo[2,1-f][1,2,4]triazin-6-yl]-carbamic acid, cis-4-aminocyclohexyl ester | 529 | 10.09 |
| 152 | cis-4-amino-4-methyl-cyclohexyl | [4-[[1-(3-fluorophenyl)methyl]-1H-indazol-5-ylamino]-5-methyl-pyrrolo[2,1-f][1,2,4]triazin-6-yl]-carbamic acid, cis-4-amino-4-methyl-cyclohexyl ester | 543 | 10.24 |
| 153 | 3-(4-hydroxy-piperidin-1-yl)-propyl | {4-[1-(3-Fluoro-benzyl)-1H-indazol-5-ylamino]-5-methyl-pyrrolo[2,1-f][1,2,4]triazin-6-yl}-carbamic acid 3-(4-hydroxy-piperidin-1-yl)-propyl ester | 573 | 9.85 |
| 154 | piperidin-4-yl | {4-[1-(3-Fluoro-benzyl)-1H-indazol-5-ylamino]-5-methyl-pyrrolo[2,1-f][1,2,4]triazin-6-yl}-carbamic acid piperidin-4-yl ester | 515 | 9.97 |
| 155 | (2R)-2-aminopropyl | [4-[[1-(3-fluorophenyl)methyl]-1H-indazol-5-ylamino]-5-methyl-pyrrolo[2,1-f][1,2,4]triazin-6-yl]-carbamic acid, (2R)-2-aminopropyl ester | 489 | 9.80 |
| 156 | (2S)-2-aminopropyl | [4-[[1-(3-fluorophenyl)methyl]-1H-indazol-5-ylamino]-5-methyl-pyrrolo[2,1-f][1,2,4]triazin-6-yl]-carbamic acid, (2S)-2-aminopropyl ester | 489 | 9.83 |

TABLE 3-continued where R = 3-fluoro-phenyl
R¹ = methyl

| Ex. # | R² | Compound Name | [M + H] | Ret Time (min) |
|---|---|---|---|---|
| 157 | (3S)-morpholin-3-ylmethyl | [4-[[1-(3-fluorophenyl)methyl]-1H-indazol-5-ylamino]-5-methyl-pyrrolo[2,1-f][1,2,4]triazin-6-yl]-carbamic acid, (3S)-3-morpholinylmethyl ester | 531 | 2.48[2] |
| 158 | (3R)-piperidin-3-yl | [4-[[1-(3-fluorophenyl)methyl]-1H-indazol-5-ylamino]-5-methyl-pyrrolo[2,1-f][1,2,4]triazin-6-yl]-carbamic acid, (3R)-3-piperidinyl ester | 515 | 10.04 |
| 159 | (3S)-piperidin-3-yl | [4-[[1-(3-fluorophenyl)methyl]-1H-indazol-5-ylamino]-5-methyl-pyrrolo[2,1-f][1,2,4]triazin-6-yl]-carbamic acid, (3S)-3-piperidinyl ester | 515 | 9.97 |
| 160 | N-Boc-(3S)-morpholin-3-ylmethyl | 3-[[[[[4-[[1-[(3-fluorophenyl)methyl]-1H-indazol-5-yl]amino]-5-methylpyrrolo[2,1-f][1,2,4]triazin-6-yl]amino]carbonyl]oxy]methyl]-4-morpholinecarboxylic acid, (3S)-1,1-dimethylethyl ester | 631 | 3.42[2] |
| 161 | benzyl | {4-[1-(3-Fluoro-benzyl)-1H-indazol-5-ylamino]-5-methyl-pyrrolo[2,1-f][1,2,4]triazin-6-yl}-carbamic acid benzyl ester | 522 | 3.48[2] |
| 162 | morpholin-3-ylmethyl | [4-[[1-(3-fluorophenyl)methyl]-1H-indazol-5-ylamino]-5-methyl-pyrrolo[2,1-f][1,2,4]triazin-6-yl]-carbamic acid, 3-morpholinylmethyl ester | 531 | 1.97[2] |
| 163 | (3R)-morpholin-3-ylmethyl | [4-[[1-(3-fluorophenyl)methyl]-1H-indazol-5-ylamino]-5-methyl-pyrrolo[2,1-f][1,2,4]triazin-6-yl]-carbamic acid, (3R)-3-morpholinylmethyl ester | 531 | 1.97[2] |

Unless otherwise indicated, HPLC Retention Times were determined using a Hypersil BDS C18 column with a 15 minute gradient time. [1]YMC TurboPack Pro column with a 2 minute gradient. [2]YMC S5 ODS column with a 4 minute gradient. [3]YMC Xterra ODS with a 2 minute gradient. [4]YMC ODS-A C18 column with a 2 minute gradient. [5]YMC C18 S5 column with a 2 minute gradient.

The following compounds were prepared using the procedure described in Example 1.

TABLE 4

| Ex. # | Structure | Compound Name | [M + H] | HPLC Ret Time (min) |
|---|---|---|---|---|
| 164 | 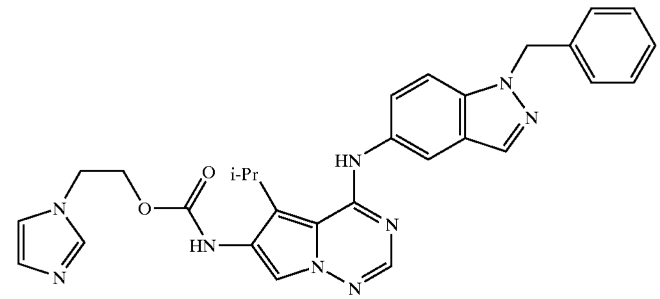 | [4-(1-Benzyl-1H-indazol-5-ylamino)-5-isopropyl-pyrrolo[2,1-f][1,2,4]triazin-6-yl]-carbamic acid 2-imidazol-1-yl-ethyl ester | 536 | 2.36[2] |
| 165 | 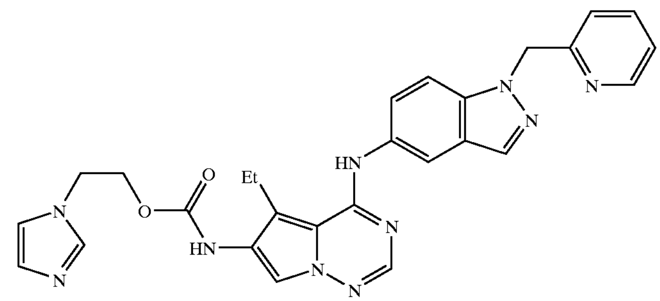 | [5-Ethyl-4-(1-pyridin-2-ylmethyl-1H-indazol-5-ylamino)-pyrrolo[2,1-f][1,2,4]triazin-6-yl]-carbamic acid 2-imidazol-1-yl-ethyl ester | 523 | 2.04[2] |
| 166 | 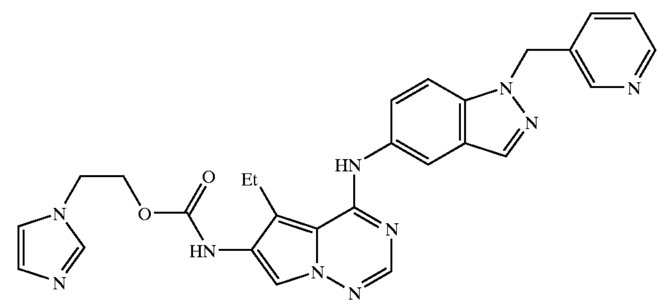 | [5-Ethyl-4-(1-pyridin-3-ylmethyl-1H-indazol-5-ylamino)-pyrrolo[2,1-f][1,2,4]triazin-6-yl]-carbamic acid 2-imidazol-1-yl-ethyl ester | 523 | 1.64[2] |
| 167 | 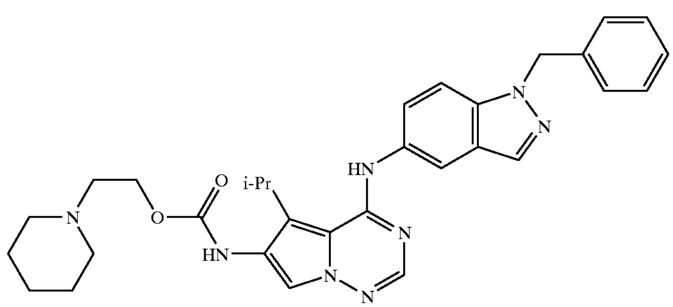 | [4-(1-Benzyl-1H-indazol-5-ylamino)-5-isopropyl-pyrrolo[2,1-f][1,2,4]triazin-6-yl]-carbamic acid 2-piperidin-1-yl-ethyl ester | 553 | 2.93[2] |
| 168 | 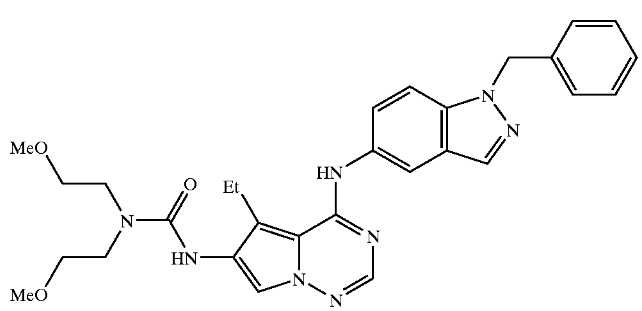 | 3-[4-(1-Benzyl-1H-indazol-5-ylamino)-5-ethyl-pyrrolo[2,1-f][1,2,4]triazin-6-yl]-1,1-bis-(2-methoxy-ethyl)-urea | 543* | 12.36 |

TABLE 4-continued

| Ex. # | Structure | Compound Name | [M + H] | HPLC Ret Time (min) |
|---|---|---|---|---|
| 169 | 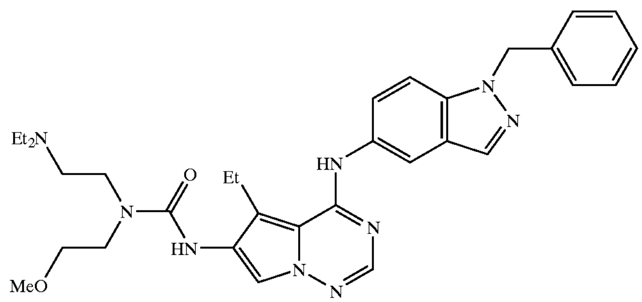 | 3-[4-(1-Benzyl-1H-indazol-5-ylamino)-5-ethyl-pyrrolo[2,1-f][1,2,4]triazin-6-yl]-1-(2-diethylamino-ethyl)-1-(2-methoxy-ethyl)-urea | 584 | 11.08 |
| 170 | 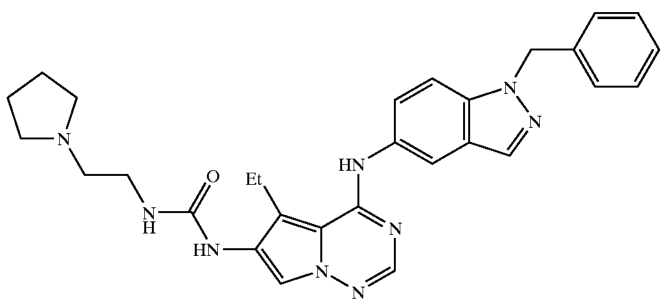 | 1-[4-(1-Benzyl-1H-5-ethyl-pyrrolo[2,1-f][1,2,4]triazin-6-yl]-3-(2-pyrrolidin-1-yl-ethyl)-urea | 524 | 10.00 |
| 171 | 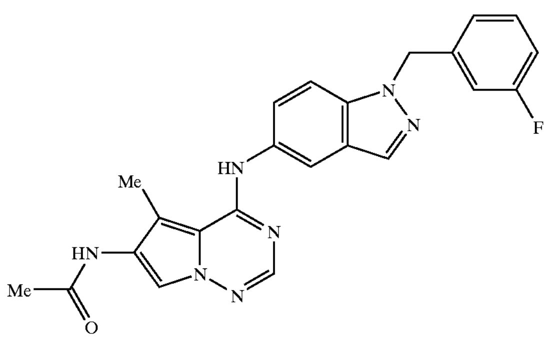 | N-{4-[1-(3-Fluoro-benzyl)-1H-indazol-5-ylamino]-5-methyl-pyrrolo[2,1-f][1,2,4]triazin-6-yl}-acetamide | 430 | 2.45 |
| 172 | 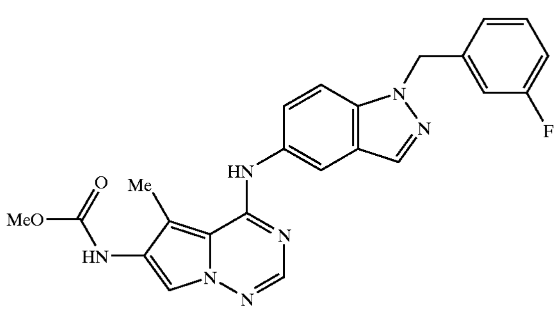 | N-{4-[1-(3-Fluoro-benzyl)-1H-indazol-5-ylamino]-5-methyl-pyrrolo[2,1-f][1,2,4]triazin-6-yl}-carbamic acid methyl ester | 446 | 2.46[2] |

TABLE 4-continued

| Ex. # | Structure | Compound Name | [M + H] | HPLC Ret Time (min) |
|---|---|---|---|---|
| 173 | 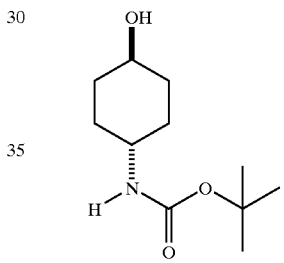 | Morpholine-3-carboxylic acid {4-[1-(3-fluoro-benzyl)-1H-indazol-5-ylamino]-5-methyl-pyrrolo[2,1-f][1,2,4]triazin-6-yl}-amide | 501 | 1.97[2] |

Unless otherwise indicated, HPLC Retention Times were determined using a Hypersil BDS C18 column with a 15 minute gradient time. [1]YMC TurboPack Pro column with a 2 minute gradient. [2]YMC S5 ODS column with a 4 minute gradient. [3]YMC Xterra ODS with a 2 minute gradient. [4]YMC ODS-A C18 column with a 2 minute gradient. [5]YMC C18 S5 column with a 2 minute gradient.

General procedures utilized for the preparation of some of the intermediates are outlined below.

Example 174

Procedure A: Preparation of (R)-(+)-3-Hydroxypiperidine-1-carboxylic acid tert-butyl ester.

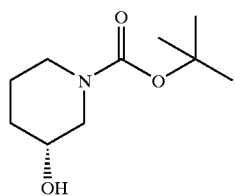

A 100 mL round bottom flask was charged with (R)-(+)-3-piperidinol hydrochloride (0.52 g, 3.77 mmol), di-tert-butyldicarbonate (0.99 g, 4.53 mmol) and $CH_2Cl_2$ (15 mL). Triethylamine (1.09 g, 10.8 mmol) was added and the solution stirred overnight. The reaction mixture was concentrated and purified by silica gel chromatography to afford 0.76 g (100%) of (R)-(+)-3-hydroxypiperidine-1-carboxylic acid tert-butyl ester as a light brown oil.

$[\alpha]_{25}^{D}$ -21.6° (c=0.1, MeOH). $^1$H NMR: δ=3.75 (m, 2H), 3.53 (m, 1H), 3.08 (m, 2H), 2.17 (bs, 1H), 1.85 (m, 1H), 1.74 (m, 1H), 1.53 (m, 2H), and 1.45 ppm (s, 9H). m/z=102 $(M-C_5H_8O_2+H)^+$.

The following derivatives were synthesized from the corresponding commercially available amino-alcohols using the above procedure: (2-Hydroxy-1,1-dimethylethyl) carbamic acid tert-butyl ester Procedure B: Preparation of trans-4-Hydroxycyclohexylcarbamic acid tert-Butyl ester.

A 1 L round bottom flask was charged with trans-4-aminocyclohexanol hydrochloride (25.0 g, 0.17 mol), di-tert-butyldicarbonate (40.8 g, 0.19 mol), and sodium hydroxide (20.1 g, 0.05 mol). Water (250 mL) and 1,4-dioxane (250 mL) were added and stirring begun. After stirring for 4 h the dioxane was removed under reduced pressure and the residue diluted with water (750 mL). The resulting solution was extracted with ethyl acetate (2×600 mL), and the combined organic phases dried over magnesium sulfate. Filtration and concentration yielded 30.6 g (74%) of 4-hydroxycyclohexylcarbamic acid tert-butyl ester as a white solid.

$^1$H NMR: δ=4.38 (bs, 1H), 3.60 (m, 1H), 3.40 (bs, 1H), 1.95 (m, 4H), 1.64 (m, 1H), 1.43 (s, 9H), 1.35 (m, 2H), and 1.16 ppm (m, 2H). m/z=116 $(M-C_5H_8O_2+H)^+$.

The following derivatives were synthesized from the corresponding commercially available amino-alcohols using the above procedure:

4-(2-Hydroxyethyl)piperazine-1-carboxylic acid tert-butyl ester

4-[2-(2-Hydroxyethoxy)ethyl]piperazine-1-carboxylic acid tert-butyl ester.

Procedure C: Preparation of 2Hydroxymethyl-piperidine-1-carboxylic acid tert-butyl ester.

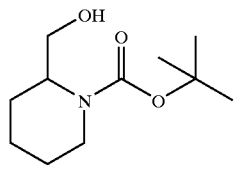

To a 50 mL round-bottomed flask was added 2-hydroxymethylpiperidine (1.0 g, 8.7 mmol), sodium bicarbonate (1.24 g, 14.8 mmol) and 15 mL of a 1:1 solution of dioxane and water. This solution was rapidly stirred as di-tert-butyl dicarbonate (2.84 g, 13 mmol, 1.5 eq.) was added. The reaction stirred for 5 hours at room temperature and the solvent was removed under reduced pressure. A mixture of 50 mL of water and 50 mL of ethyl acetate was added to the residue and the layers were separated. The aqueous layer was extracted with ethyl acetate (2×50 mL) and the combined organic layers were dried over sodium sulfate. The suspension was filtered and concentrated giving a clear oil which was then purified by silica gel chromatography. This afforded 1.56 g (84%) of 2-hydroxymethyl-piperidine-1-carboxylic acid tert-butyl ester as a white solid. Mpt.=72–73° C. $^1$H NMR δ=4.28 (m, 1H), 3.93 (m, 1H), 3.77 (m, 1H), 3.60 (m, 1H), 2.96 (m, 1H), 2.39 (s, 1H) and 1.76–1.30 ppm (m, 15H). m/z=116 (M−C$_5$H$_8$O$_2$+H)$^+$.

The following derivatives were synthesized from the corresponding commercially available amino-alcohols using the above procedure:

4-(2-Hydroxyethyl)piperidine-1-carboxylic acid tert-butyl ester

3-Hydroxymethylpiperidine-1-carboxylic acid tert-butyl ester

4-Hydroxymethylpiperidine-1-carboxylic acid tert-butyl ester

The following alcohols were synthesized via the given literature procedures (all of which are herein incorporated by reference).

1-Imidazoleethanol and 1-Pyrazoleethanol: Banfi, A.; Sala, A.; Soresinetti, P. A.; Russo, G. *J. Heterocyclic Chem.* 1990, 27, 215.

4-Methyl-1-piperazineethanol: Cymerman-Craig, J.; Harrison, R. J.; Tate, M. E.; Thorp, R. H.; Ladd, R. *Aust. J. Chem.* 1956, 9 89.

4-Morpholinepropanol: Chini, M.; Crotti, P.; Favero, L.; Macchia, F. *Tetrahedron Lett.* 1994, 35, 761.

2-(2-Hydroxyethyl)imidazole: Lawson, J. Keith, J. R. *J. Am. Chem. Soc.* 1953, 75, 3398.

[2-(2-Hydroxyethoxy)ethyl]carbamic acid tert-butyl ester: Greenwald, R. B.; Choe, Y. H.; Conover, C. D.; Shum, K.; Wu, D.; Royzen, M. *J. Med. Chem.* 2000, 43, 475.

(S)-2-Hydroxymethylmorpholine and (R)-2-hydroxymethylmorpholine: Berg, S.; Larsson, L.; Renyi, L.; Ross, S. B.; Thorberg, S.; Thorell-Svantesson, G. *J. Med. Chem.* 1998, 41, 1934. These amino-alcohols were converted to (S)-2-Hydroxymethyl-morpholine-4-carboxylic acid tert-butyl ester (R)-2-Hydroxymethyl-morpholine-4-carboxylic acid tert-butyl ester by Procedure A above.

cis-4-Amino-4-methylcyclohexanol: Gelotte, K. O.; Surrey, A. R. U.S. Pat. No. 3,895,036, 1975. This amino-alcohol was converted to 4-Hydroxy-1-methylcyclohexylcarbamic acid tert-butyl ester by Procedure A above.

4-(3-Hydroxypropyl)piperidine-1-carboxylic acid tert-butyl ester: Egbertson, M. S.; Chang, C. T.-C., Duggan, M. E.; Gould, R. J.; Halczenko, W.; Hartman, G. D.; Laswell, W. L.; Jynch, J. J.; Lynch, R. J.; Manno, P. D.; Naylor, A. M.; Prugh, J. D.; Ramkit, D. R.; Sitko, G. R.; Smith, R. S.; Turchi, L. M.; Zhang, G. *J. Med. Chem.* 1994, 37, 2537.

1-(2-Hydroxyethyl)-1,2,4-triazole: Aisworth, C.; Jones, R. G. *J. Am. Chem. Soc.* 1955, 77, 621.

2-Hydroxymethyl-1-methylimidazole: Hay, M. P.; Wilson, W. R.; Denny, W. A. *Tetrahedron* 2000, 56, 645.

(R)-3-Hydroxymethylpyrrolidine and (S)-3-Hydroxymethylpyrrolidine: Culbertson, T. P.; Domagala, J. M.; Nichols, J. B.; Priebe, S.; Skeean, R. W. *J. Med. Chem.* 1987, 30, 1715. These amino-alcohols were converted to (R)-3-Hydroxymethylpyrrolidine-1-carboxylic acid tert-butyl ester and (S)-3-Hydroxymethyl-pyrrolidine-1-carboxylic acid tert-butyl ester by Procedure A above.

(S)-(−)-3-Hydroxypiperidine: Olsen, R. K.; Bhat, K. L.; Wardle, R. B.; Hennen, W. J.; Kini, G. D. *J. Org. Chem.* 1985, 50, 896. This amino-alcohol was converted (S)-(−)-3-Hydroxypiperidine-1-carboxylic acid tert-butyl ester by Procedure A above.

The general procedure outlined below may be used to prepare the compounds disclosed in Examples 1, 92, 136–144, 157, 162 and 163.

Example 175

A. Preparation of N-benzyl-serine

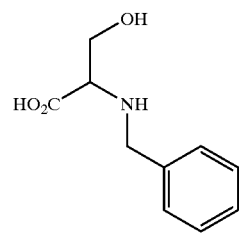

To a reaction vessel was added solid serine methyl ester hydrochloride (1 eq). Methanol (2.85 vol) was added and agitation was started. Triethylamine (1 eq) was added over 10 min while maintaining the temperature at 14~18° C. Stirring was continued until all solids dissolved. The mixture was cooled to 10° C. and benzaldehyde (1 eq) was added over 15 min while maintaining the temperature between 11~15° C. The reaction was held for 30 min at 8~12° C. Solid sodium borohydride (4 eq) was added over 2 hr while maintaining the temperature at 10~20° C. The reaction was held for 30 min at 14~16° C. In a separate flask, methanol (1.15 vol) and water (1.72 vol) were added. Sodium hydroxide, 50 wt/wt % in water (3 eq) was added and the resulting solution was cooled to 15° C. The Schiff's base was transferred to this mixture over 1 hr maintaining the internal temperature between 16~22° C. Water was added (1.72 vol), followed by concentrated HCl, 2.2 M in water (2.67 eq) while maintaining the temperature at 15~25° C. to adjust the pH to 9.5. The mixture was filtered and the filter-cake was washed with two portions of water (0.58 vol). The combined aqueous portions were washed two times with ethyl acetate (5.75 vol). The mixture was cooled from 25° C. to 15° C., and concentrated HCl was added, 12.2 M in water (0.89 eq), until the pH of the mixture reached 6.5, while maintaining the temperature between 17–22° C. The mixture was held for 15~25 hr at 5° C. and then the solids were collected on a filter funnel. The filter-cake was washed with two portions of water (1.43 vol) and two portions of heptane (1.43 vol). The wet solid was transferred to a drying tray, and dried at 45° C. for 21 h to afford the product.

B. Preparation of Compound B

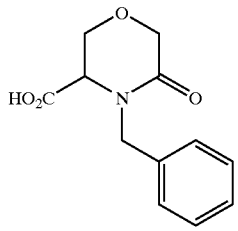

To a reactor was charged N-benzyl-serine (1 eq) and THF (6.1 vol). The resulting solution was cooled to 0±5° C. and a pre-cooled solution (0–5° C.) of potassium carbonate (3 eq) in water (6.1 vol) was added. Chloroacetyl chloride (1.4 eq) then was added via addition funnel while maintaining the internal temperature below 5° C. The biphasic reaction mixture was aged for approximately 30 min at 0±5° C. After aging, the mixture was sampled for HPLC analysis. If >6 area percent remaining N-benzyl-serine was present, additional chloroacetyl chloride was added according to the following formula: for every 10 area percent N-benzyl-serine, add 0.12–0.15 equivalents chloroacetyl chloride. If an additional chloroacetyl chloride charge was necessary, allow the mixture to age an additional 30 min after the charge, and resample. Once the reaction completeness specification has been met, charge 50 wt % sodium hydroxide while keeping the internal temperature between 5 and 10° C. until the pH remains constant >13.5. The reaction was deemed complete when HPLC analysis showed <1 area percent (combined) intermediates. The mixture was warmed to 25° C., and heptane (2 vol) was added. The mixture was stirred rapidly for 10 min, and the phases are allowed to separate. The organic phase was discarded, and the rich aqueous phase was treated again with heptane (3 vol). After stirring rapidly 10 min, the phases were allowed to settle, and the organic phase was discarded. The rich aqueous portion was cooled to −5–0° C. and 37 wt % hydrochloric acid (aq) was added while maintaining a batch temperature <10° C. until pH <2. The resulting slurry was kept at −10–0° C. for a minimum of 4 h. The slurry was then filtered and washed with pre-cooled (3–7° C.) water (2×4.6 vol). The wet cake was dried in vacuo at 40–45° C. to afford the desired product.

C. Preparation of (4-benzyl-morpholin-3-yl)]-methanol hydrochloride

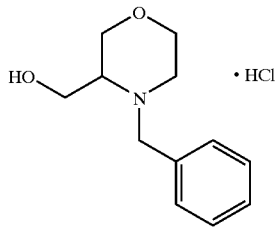

To a stirred mixture of compound B (1 eq) in dry THF (16 vol) under nitrogen was added triethyl amine (1.2 eq). To this mixture was added borane-methyl sulfide complex (7.5 eq) at such a rate that the temperature of the reaction mixture was kept below 10° C. The reaction mixture was gently refluxed (65° C.) under nitrogen for 5.5 h. The mixture was cooled and MeOH (1.39 vol) was added slowly. The internal temperature was kept below 25° C. during the addition. To the resulting mixture was added water (4.2 vol) and the mixture was stirred at room temperature overnight. The mixture was concentrated in vacuo and diluted with 2N aqueous sodium hydroxide (4.6 eq) and water (1.8 vol). The mixture was extracted with ethyl acetate (2×7 vol). The combined ethyl acetate extracts were washed with a 20% aqueous sodium chloride solution (4.2 vol). The ethyl acetate extracts were then concentrated in vacuo to give a crude oil. The oil was diluted with ethyl acetate (10.2 vol) and methanol (0.5 vol). To this solution was added trimethylsilyl chloride (0.6 vol) dropwise until the pH of the solution was acidic. The batch temperature during the trimethylsilyl chloride addition temperature was kept below 20° C. At the end of the addition, the mixture was cooled at 0° C. for 2 h and the precipitate was collected by filtration to give the desired product.

D. Preparation of 3-(hydroxymethyl)-morpholine-4-carboxylic acid tert-butyl ester

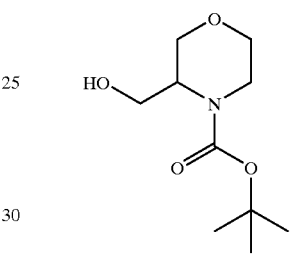

A mixture of (4-benzyl-morpholin-3-yl)]-methanol hydrochloride (1 eq), aqueous $K_3PO_4$ (2.5 eq), and EtOAc was stirred until homogeneous. The EtOAc layer was separated, and the aqueous layer was extracted with fresh EtOAc. The combined EtOAc layers were charged into a flask containing 20 wt % $Pd(OH)_2$/C (0.06 eq). Di-tert-butyl dicarbonate (1 eq) was added. The mixture was hydrogenated for 4 h at 15 psi. After it was found complete by HPLC, the mixture was filtered through Celite. The product was crystallized from cyclohexane (7–10 volumes) to afford the title compound.

E. Preparation of the Indazole

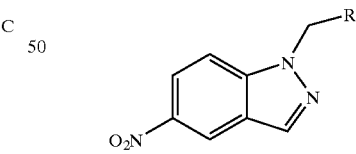

5-nitro indazole (1 eq), cesium carbonate (1.1 eq) and DMF (5 vol) were heated to 70–80° C. The appropriate bromide $RCH_2Br$ (1 eq) was charged over 75 min. The reaction mixture was cooled to 20° C. The salts were filtered and the cake was washed with DMF (2.7 vol). The product was crystallized by charging water (1.35 to 1.45 vol) between 15–21° C. The crystal slurry was held for 4 h, the crystals were filtered and washed with a 2:1 DMF:water mixture (2.1 vol), water (2 vol) and finally 3:1 cold acetonitrile:water mixture (1.5 vol). The wet cake was dried at 45° C. to afford the product E.

F. Preparation of the Indazole Amine

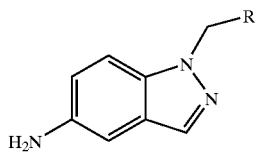

The indazole E (1 eq) was charged to the hyrdogenator, THF (8 vol)was added and hydrogenated at 15 psi between 30–40° C. The reaction mixture was held for ~1 h (s.m. <3% by HPLC), cooled to 25° C., and the catalyst was filtered and washed with THF (0.9 vol). The reaction mixture was transferred to another vessel, rinsed again with THF (0.4 vol), distilled to the desired volume (5.5 vol) atmospherically, and heptane was added(15 vol). The reaction mixture was kept between 47–60° C. over 1 h. The slurry was cooled over 1.5 h to 18–23° C. The slurry was held for 1 h, filtered, washed with THF/heptane (1:4, 10 vol) and dried in oven at 45° C.

G. Preparation of the Ester

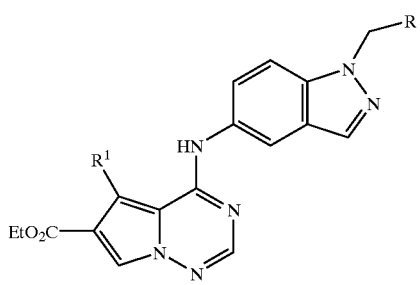

A 3-neck flask was charged with 5-alkyl-4-oxo-3,4-dihydr-pyrrolo[2,1-f][1,2,4]triazine-6-carboxylic acid ethyl ester (1 eq) and dry toluene (15 vol). POCl$_3$ (1.2 eq) was added in one portion, followed by slow addition of diisopropylethylamine (1.1 eq) at a rate that maintained the temperature below 30° C. The resulting suspension was heated to 111° C. for 24 h becoming homogeneous at about 80° C. The reaction was monitored by HPLC after quenching with 2 M MeNH$_2$/THF (10 μL reaction mixture, 20 μL MeNH$_2$/THF in 200 μL acetonitrile). Upon completion, the reaction was cooled to -2° C. and was added to a solution of K$_2$HPO$_4$ (4 eq) in H$_2$O (16 vol) while maintaining temperature below 10° C. The reaction mixture was stirred for 20 min at -22° C. The resulting light suspension was filtered through a pad of celite and the layers were separated. The organic layer was washed with 23.5 wt % K$_2$HPO$_4$ in H$_2$O (3 vol), followed by water (2.5 vol). The solution was filtered and concentrated by heating over the temperature range of 22° C. to 58° C.; continuing until the HPLC ratio of toluene to the starting ester is 26–36%. The reaction mixture was cooled from 58° C. to 40–50° C. To the resulting suspension was added the indazole F (0.988 eq) and diisopropylethylamine (1.1 eq). The reaction was heated to 70–80° C. and held at this temperature until it was shown complete by HPLC. It was then cooled to 55° C. and isopropyl alcohol (15.5 vol) was added. The reaction mixture was cooled from 55° C. to 22° C. over a period of 1.8~2.2 hr. and filtered. The filter cake was washed with cold isopropyl alcohol (5.5 vol) and dried under vacuum below 50° C. to afford the product.

H. Preparation of the Acid

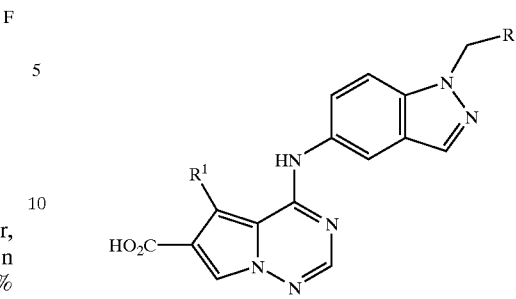

A flask equipped with mechanical stirrer was charged with the ester G (1 eq), THF (4 vol) and MeOH (2.5 vol). The suspension was cooled to 5° C. and 50% NaOH (5.3 eq) solution was slowly added maintaining the temperature below 15° C. The resulting solution was warmed to 60° C. for 4 h, then cooled to 25° C. The reaction mixture was charged with THF (7 vol), and concentrated HCl (9.95 eq) was slowly added while maintaining the temperature below 35° C. to pH 3. The resulting slurry was stirred at ambient temperature overnight, then filtered. The filter cake was washed with H$_2$O (3×5 vol) and dried on the filter for 1 h. The cake was washed with heptane (1 vol) and dried under vacuum at 50° C. to afford the product.

I. Preparation of the Protected Carbamate

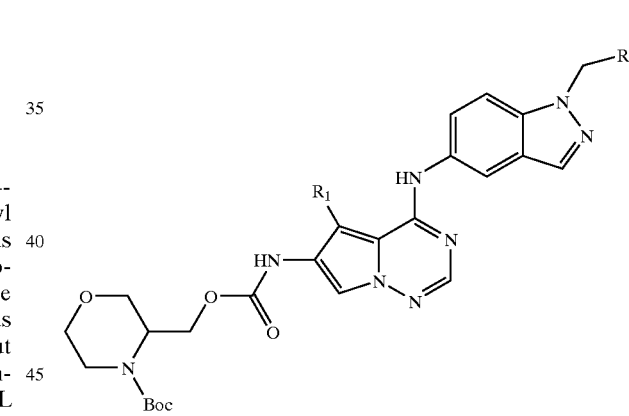

A flask was charged with the carboxylic acid H (1 eq) and toluene (15 vol). Residual water was removed by azeotropic distillation and the supernatant was analyzed for water content (KF: <200 ppm water). The flask was then charged with 3-hydroxymethyl-morpholine-4-carboxylic acid tert-butyl ester (0.96 eq) at ~77° C. Triethyl amine (1.2 eq) and diphenylphosphoryl azide (1.2 eq) were added between 77–85° C. The reaction was cooled to 25° C., diluted with THF (15 vol) and washed with 10% K$_2$CO$_3$ (10 vol), saturated NaCl (10 vol) and water (10 vol) respectively. The rich organic was polish filtered and distilled at atmospheric pressure till the pot temperature was >100° C. The final volume was adjusted to 15 volumes by adding toluene if necessary. The mixture was cooled to 80° C., water (1 eq) was added and the product was crystallized. The slurry was cooled to 25° C. over 1 h and held for 17 h. The solid was collected by filtration and the filter cake was rinsed with toluene (2×2 vol). The solid was air dried overnight and then dried under vacuum at 50° C. to give the product.

J. Preparation of the Carbamate

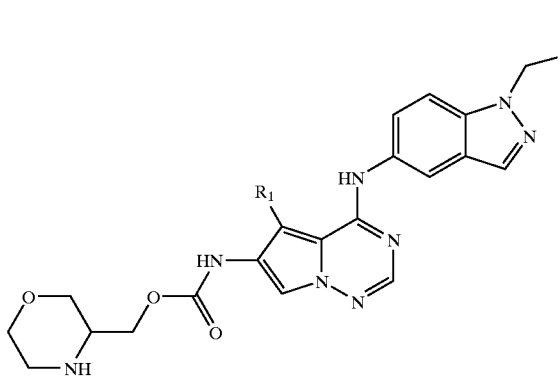

A flask was charged with the carbamate I (1 eq), water (7 vol), methanol (1 vol) and concentrated HCl solution (5 eq)). The slurry was heated to 70° C. and held at this temperature until complete conversion to the desired product by HPLC. After completion, water (3 vol) was charged into the hot reaction mixture, and cooled the mixture to 45–55° C. The mixture was filtered and the filtrate was extracted with ethyl acetate (2×6 vol). Ethyl acetate (10 vol), methanol (2–3 vol) and butylhydroxyanisole (2.7 wt %) were charged into the isolated aqueous phase. Using 50% NaOH solution, the pH of the mixture was adjusted to pH 9–13. The phases were allowed to separate. The product rich organic layer was collected and water (10 vol) was added into the mixture at 55–60° C. in 15–30 min. The mixture was held at 55–60° C. for 30 min after addition of water, then cooled to 19–25° C. over 1 h. The product was filtered and washed with ethyl acetate (2×3 vol). The filter cake was reslurried with ethyl acetate (15 vol) and butylhydroxyanisole (2.7 wt %) was added. The resulting slurry was distilled at atmospheric pressure. The volume of the mixture was adjusted to 8–10 volumes while maintaining the temperature at 74–78° C. The temperature was cooled to 19–25° C. over an hour. The solid was collected by filtration and the filter cake was rinsed with ethyl acetate (2.2 vol). The solid was dried under vacuum at 45° C. to afford the desired compound.

What is claimed is:

1. A compound of formula I

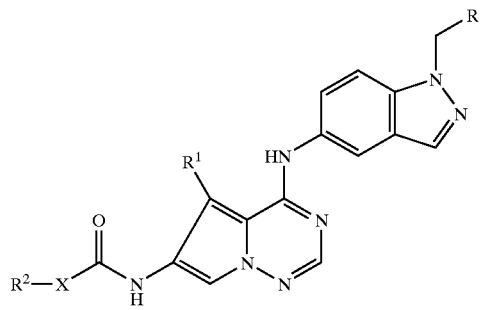

wherein
R is selected from the group consisting of aryl, substituted aryl, heterocyclo, and substituted heterocyclo;
$R^1$ is selected from the group consisting of alkyl and substituted alkyl;
$R^2$ is selected from the group consisting of hydrogen, alkyl, substituted alkyl, cycloalkyl, substituted cycloalkyl, aryl, substituted aryl, aralkyl, heterocyclo, and substituted heterocyclo; or, $R^2$ may be absent;
X is selected from the group consisting of a bond, O, S, $C(R^3)_2$, $C(R^3)_3$, $NR^3$; and $N(R^3)_2$;
$R^3$ is independently selected from the group consisting of hydrogen, alkyl, substituted alkyl, aryl, substituted aryl, aralkyl, heterocyclo, and substituted heterocyclo, or a pharmaceutically acceptable salt, enantiomer and diastereomer thereof.

2. The compound according to claim 1 wherein R is aryl or substituted aryl and $R^1$ is a lower alkyl group.

3. The compound according to claim 2 wherein X is —O— and $R^2$ is cycloalkyl, substituted cycloalkyl, heterocyclo or substituted heterocyclo.

4. The compound according to claim 3 wherein R is phenyl or substituted phenyl and $R^1$ is methyl or ethyl.

5. A compound selected from the group consisting of
[5-ethyl-4-[[(1-phenylmethyl)-1H-indazol-5-yl]amino]pyrrolo[2,1-f][1,2,4]triazin-6-yl]-carbamic acid, (3S)-3-morpholinylmethyl ester,
[5-ethyl-4-[[(1-phenylmethyl)-1H-indazol-5-yl]amino]pyrrolo[2,1-f][1,2,4]triazin-6-yl]-carbamic acid, (2R)-2-pyrrolidinylmethyl ester,
[5-ethyl-4-[[(1-phenylmethyl)-1H-indazol-5-yl]amino]pyrrolo[2,1-f][1,2,4]triazin-6-yl]-carbamic acid, (2S)-2-pyrrolidinylmethyl ester,
[5-ethyl-4-[[(1-phenylmethyl)-1H-indazol-5-yl]amino]pyrrolo[2,1-f][1,2,4]triazin-6-yl]-carbamic acid, (3R)-3-morpholinylmethyl ester,
[5-ethyl-4-[[(1-phenylmethyl)-1H-indazol-5-yl]amino]pyrrolo[2,1-f][1,2,4]triazin-6-yl]-carbamic acid, 3-[(3S)-3-hydroxy-1-pyrrolidinyl]propyl ester,
[5-ethyl-4-[[(1-phenylmethyl)-1H-indazol-5-yl]amino]pyrrolo[2,1-f][1,2,4]triazin-6-yl]-carbamic acid, 3-[(3S)-3-hydroxy-1-piperidinyl]propyl ester,
[5-ethyl-4-[[(1-phenylmethyl)-1H-indazol-5-yl]amino]pyrrolo[2,1-f][1,2,4]triazin-6-yl]-carbamic acid, (3R)-3-pyrrolidinylmethyl ester,
[5-ethyl-4-[[(1-phenylmethyl)-1H-indazol-5-yl]amino]pyrrolo[2,1-f][1,2,4]triazin-6-yl]-carbamic acid, 3-[(3R)-3-hydroxy-1-pyrrolidinyl]propyl ester,
[5-ethyl-4-[[(1-phenylmethyl)-1H-indazol-5-yl]amino]pyrrolo[2,1-f][1,2,4]triazin-6-yl]-carbamic acid, [(2S)-1-methyl-2-pyrrolidinyl]methyl ester,
[5-ethyl-4-[[(1-phenylmethyl)-1H-indazol-5-yl]amino]pyrrolo[2,1-f][1,2,4]triazin-6-yl]-carbamic acid, (2S)-2-morpholinylmethyl ester,
[5-ethyl-4-[[(1-phenylmethyl)-1H-indazol-5-yl]amino]pyrrolo[2,1-f][1,2,4]triazin-6-yl]-carbamic acid, (3S)-3-pyrrolidinylmethyl ester,
[5-ethyl-4-[[(1-phenylmethyl)-1H-indazol-5-yl]amino]pyrrolo[2,1-f][1,2,4]triazin-6-yl]-carbamic acid, (2R)-2-morpholinylmethyl ester,
[5-ethyl-4-[[(1-phenylmethyl)-1H-indazol-5-yl]amino]pyrrolo[2,1-f][1,2,4]triazin-6-yl]-carbamic acid, [(3R)-1-methyl-3-pyrrolidinyl]methyl ester,
[5-ethyl-4-[[(1-phenylmethyl)-1H-indazol-5-yl]amino]pyrrolo[2,1-f][1,2,4]triazin-6-yl]-carbamic acid, trans-4-aminocyclohexyl ester,
[5-ethyl-4-[[(1-phenylmethyl)-1H-indazol-5-yl]amino]pyrrolo[2,1-f][1,2,4]triazin-6-yl]-carbamic acid, (3R)-3-piperidinyl ester,
[5-ethyl-4-[[(1-phenylmethyl)-1H-indazol-5-yl]amino]pyrrolo[2,1-f][1,2,4]triazin-6-yl]-carbamic acid, (3S)-3-piperidinyl ester,
[5-ethyl-4-[[(1-phenylmethyl)-1H-indazol-5-yl]amino]pyrrolo[2,1-f][1,2,4]triazin-6-yl]-carbamic acid, cis-4-aminocyclohexyl,

[5-ethyl-4-[[(1-phenylmethyl)-1H-indazol-5-yl]amino]pyrrolo[2,1-f][1,2,4]triazin-6-yl]-carbamic acid, (2R,4R)-2-(hydroxymethyl)-4-piperidinyl ester,

[5-ethyl-4-[[(1-phenylmethyl)-1H-indazol-5-yl]amino]pyrrolo[2,1-f][1,2,4]triazin-6-yl]-carbamic acid, (2S)-2-(hydroxymethyl)-4-piperidinyl ester,

[5-ethyl-4-[[(1-phenylmethyl)-1H-indazol-5-yl]amino]pyrrolo[2,1-f][1,2,4]triazin-6-yl]-carbamic acid, cis-4-(aminomethyl)cyclohexyl ester,

[5-ethyl-4-[[(1-phenylmethyl)-1H-indazol-5-yl]amino]pyrrolo[2,1-f][1,2,4]triazin-6-yl]-carbamic acid, cis-4-amino-4-methylcyclohexyl ester,

[5-ethyl-4-[[(1-phenylmethyl)-1H-indazol-5-yl]amino]pyrrolo[2,1-f][1,2,4]triazin-6-yl]-carbamic acid, [(2R,4R)-4-(hydroxy-2-piperidinyl]methylester,

[5-ethyl-4-[[(1-phenylmethyl)-1H-indazol-5-yl]amino]pyrrolo[2,1-f][1,2,4]triazin-6-yl]-carbamic acid, trans-4-(aminomethyl)cyclohexyl ester,

[5-ethyl-4-[[1-(2-oxazolylmethyl)-1H-indazol-5-yl]amino]pyrrolo[2,1-f][1,2,4]triazin-6-yl]-carbamic acid, (3S)-3-morpholinylmethyl ester,

[5-ethyl-4-[[1-(2-thienylmethyl)-1H-indazol-5-yl]amino]pyrrolo[2,1-f][1,2,4]triazin-6-yl]-carbamic acid, (3S)-3-morpholinylmethyl ester,

[5-ethyl-4-[[1-[(3-fluorophenyl)methyl]-1H-indazol-5-yl]amino]pyrrolo[2,1-f][1,2,4]triazin-6-yl]-carbamic acid, (3S)-3-morpholinylmethyl ester,

[5-ethyl-4-[[1-(4-thiazolylmethyl)-1H-indazol-5-yl]amino]pyrrolo[2,1-f][1,2,4]triazin-6-yl]-carbamic acid, (3S)-3-morpholinylmethyl ester,

[5-ethyl-4-[[1-(3-thienylmethyl)-1H-indazol-5-yl]amino]pyrrolo[2,1-f][1,2,4]triazin-6-yl]-carbamic acid, (3S)-3-morpholinylmethyl ester,

[5-ethyl-4-[[1-(2-pyridinylmethyl)-1H-indazol-5-yl]amino]pyrrolo[2,1-f][1,2,4]triazin-6-yl]-carbamic acid, (3S)-3-morpholinylmethyl ester,

[5-ethyl-4-[[1-(2-thiazolylmethyl)-1H-indazol-5-yl]amino]pyrrolo[2,1-f][1,2,4]triazin-6-yl]-carbamic acid, (3S)-3-morpholinylmethyl ester,

[5-ethyl-4-[[1-(3-pyridinylmethyl)-1H-indazol-5-yl]amino]pyrrolo[2,1-f][1,2,4]triazin-6-yl]-carbamic acid, (3S)-3-morpholinylmethyl ester,

[5-ethyl-4-[[1-(pyrazinylmethyl)-1H-indazol-5-yl]amino]pyrrolo[2,1-f][1,2,4]triazin-6-yl]-carbamic acid, (3S)-3-morpholinylmethyl ester,

[4-[[1-(3-fluorophenyl)methyl]-1H-indazol-5-ylamino]-5-methyl-pyrrolo[2,1-f][1,2,4]triazin-6-yl]-carbamic acid, trans-4-aminocyclohexyl ester,

[4-[[1-(3-fluorophenyl)methyl]-1H-indazol-5-ylamino]-5-methyl-pyrrolo[2,1-f][1,2,4]triazin-6-yl]-carbamic acid, (2R,4R)-2-(hydroxymethyl)-4-piperidinyl ester,

[4-[[1-(3-fluorophenyl)methyl]-1H-indazol-5-ylamino]-5-methyl-pyrrolo[2,1-f][1,2,4]triazin-6-yl]-carbamic acid, (2S,4S)-2-(hydroxymethyl)-4-piperidinyl ester,

[4-[[-1-(3-fluorophenyl)methyl]-1H-indazol-5-ylamino]-5-methyl-pyrrolo[2,1-f][1,2,4]triazin-6-yl]-carbamic acid, cis-4-aminocyclohexyl ester,

[4-[[1-(3-fluorophenyl)methyl]-1H-indazol-5-ylamino]-5-methyl-pyrrolo[2,1-f][1,2,4]triazin-6-yl]-carbamic acid, cis-4-amino-4-methyl-cyclohexyl ester,

[4-[[1-(3-fluorophenyl)methyl]-1H-indazol-5-ylamino]-5-methyl-pyrrolo[2,1-f][1,2,4]triazin-6-yl]-carbamic acid, (2R)-2-aminopropyl ester,

[4-[[1-(3-fluorophenyl)methyl]-1H-indazol-5-ylamino]-5-methyl-pyrrolo[2,1-f][1,2,4]triazin-6-yl]-carbamic acid, (2S)-2-aminopropyl ester,

[4-[[1-(3-fluorophenyl)methyl]-1H-indazol-5-ylamino]-5-methyl-pyrrolo[2,1-f][1,2,4]triazin-6-yl]-carbamic acid, (3S)-3-morpholinylmethyl ester,

[4-[[1-(3-fluorophenyl)methyl]-1H-indazol-5-ylamino]-5-methyl-pyrrolo[2,1-f][1,2,4]triazin-6-yl]-carbamic acid, (3R)-3-piperidinyl ester,

[4-[[1-(3-fluorophenyl)methyl]-1H-indazol-5-ylamino]-5-methyl-pyrrolo[2,1-f][1,2,4]triazin-6-yl]-carbamic acid, (3S)-3-piperidinyl ester, 3-[[[[[4-[[1[(3-fluorophenyl)methyl]-1H-indazol-5-yl]amino]-5-methylpyrrolo[2,1-f][1,2,4]triazin-6-yl]amino]carbonyl]oxy]methyl]-4-morpholinecarboxylic acid, (3S)-1,1-dimethylethyl ester,

[4-[[1-(3-fluorophenyl)methyl]-1H-indazol-5-ylamino]-5-methyl-pyrrolo[2,1-f][1,2,4]triazin-6-yl]-carbamic acid, 3-morpholinylmethyl ester, and

[4-[[1-(3-fluorophenyl)methyl]-1H-indazol-5-ylamino]-5-methyl-pyrrolo[2,1-f][1,2,4]triazin-6-yl]-carbamic acid, (3R)-3-morpholinylmethyl ester;

or a pharmaceutically acceptable salt thereof.

6. A compound of claim 1 having an $IC_{50}$ value of less than 5 μM for HER kinase assay selected from the group consisting of HER1, HER2 and HER4.

7. A compound of claim 1 having an $IC_{50}$ value of less than 1 μM for HER kinase assay selected from the group consisting of HER1, HER2 and HER4.

8. A compound of claim 1 having an $IC_{50}$ value of less than 0.1 μM for HER kinase assay selected from the group consisting of HER1, HER2 and HER4.

9. A pharmaceutical composition comprising a compound of claim 1 and a pharmaceutically acceptable carrier.

10. A method for treating rheumatoid arthritis comprising administering to a warm-blooded species in need thereof, a therapeutically effective amount of a compound of claim 1.

* * * * *